United States Patent
Meriño et al.

(10) Patent No.: US 9,862,936 B2
(45) Date of Patent: Jan. 9, 2018

(54) METHODS OF PURIFYING ADENO-ASSOCIATED VIRUS (AAV) AND/OR RECOMBINANT ADENO-ASSOCIATED VIRUS (RAAV) AND GRADIENTS AND FLOW-THROUGH BUFFERS THEREFORE

(71) Applicants: ALFA WASSERMANN, INC., West Caldwell, NJ (US); VIROVEK, INC., Hayward, CA (US)

(72) Inventors: Sandra Patricia Meriño, Weesp (NL); Haifeng Chen, Piedmont, CA (US)

(73) Assignees: ALFA WASSERMANN, INC., West Caldwell, NJ (US); VIROVEK, INC., Hayward, CA (US)

( * ) Notice: Subject to any disclaimer, the term of this patent is extended or adjusted under 35 U.S.C. 154(b) by 0 days.

(21) Appl. No.: 14/991,510

(22) Filed: Jan. 8, 2016

(65) Prior Publication Data

US 2016/0201086 A1    Jul. 14, 2016

Related U.S. Application Data

(60) Provisional application No. 62/102,645, filed on Jan. 13, 2015, provisional application No. 62/102,650, filed on Jan. 13, 2015, provisional application No. 62/139,242, filed on Mar. 27, 2015.

(51) Int. Cl.
*B01D 21/26* (2006.01)
*H01B 1/06* (2006.01)
*C12N 7/00* (2006.01)

(52) U.S. Cl.
CPC ...... *C12N 7/00* (2013.01); *C12N 2750/14151* (2013.01)

(58) Field of Classification Search
None
See application file for complete search history.

(56) References Cited

U.S. PATENT DOCUMENTS

| | | | |
|---|---|---|---|
| 3,430,849 A | 3/1969 | Gibson et al. |
| 6,146,874 A | 11/2000 | Zolotukhin et al. |
| 6,194,191 B1 | 2/2001 | Zhang et al. |
| 6,485,958 B2 | 11/2002 | Blanche et al. |
| 6,593,123 B1 | 7/2003 | Wright et al. |
| 6,660,514 B1 | 12/2003 | Zolotukhin et al. |
| 6,905,862 B2 | 6/2005 | Blanche et al. |
| 6,989,264 B2 | 1/2006 | Atkinson et al. |
| 7,326,555 B2 | 2/2008 | Konz, Jr. et al. |
| 7,419,817 B2 | 9/2008 | Chiorini et al. |
| 7,837,609 B2 | 11/2010 | Merino et al. |
| 2004/0121444 A1 | 6/2004 | Zolotukhin et al. |
| 2005/0189305 A1 | 9/2005 | Forrester et al. |
| 2005/0272029 A1 | 12/2005 | Saunier et al. |
| 2006/0035364 A1 | 2/2006 | Wright et al. |
| 2006/0266715 A1 | 11/2006 | Loewy et al. |
| 2008/0019959 A1* | 1/2008 | Becher ............... C12N 9/94 424/94.21 |
| 2008/0118970 A1 | 5/2008 | Konz, Jr. et al. |
| 2008/0206812 A1 | 8/2008 | Atkinson et al. |
| 2009/0023197 A1 | 1/2009 | Brass et al. |
| 2009/0275107 A1 | 11/2009 | Lock et al. |
| 2013/0072548 A1 | 3/2013 | Wright et al. |
| 2014/0242671 A1 | 8/2014 | Grieger et al. |

FOREIGN PATENT DOCUMENTS

| | | |
|---|---|---|
| EP | 1284287 A1 | 2/2003 |
| WO | 2004083405 A2 | 9/2004 |

OTHER PUBLICATIONS

Beckman Type 70 Ti Rotor datasheet (2008).*
Wright et al. Mol Ther 2005;12:171-8.*
Miranda et al. book chapter in COLOSS, 2013.*
Okuda et al. J Clin Microbiol 1975;96-101.*
Segura et al. J Virol Methods 2006;133:82-91.*
Lawrence et al. MAVE 2010; Chapter 17: pp. 166-181.*
Lock et al. Hum Gene Ther 2010;21:1259-71.*
International Search Report dated Jul. 21, 2016 from corresponding International PCT Application No. PCT/US16/12680; 3 pages.
Written Opinion dated Jul. 21, 2016 from corresponding International PCT Application No. PCT/US16/12680; 8 pages.
Alfa Wassermann, Inc.; "Separation Technologies; PROMATIX 1000 Laboratory Ultracentrifuge brochure"; Ultracentrifugation Bioprocess, 2003.
Anderson et al.; "Continuous-Flow Centrifugation Combined With Isopyonic Banding Rotors B-VIII and B-IX"; National Cancer Institute Monograph No. 21; 1966.
Elliott et al.; "Continuous-Flow Ultracentrifugation of Canine Distemper Virus and Infectious Canine Hepatitis Virus"; Appl. Microbiol. 1970, 20(5): 667, http://aem.asm.org.
Gias, E et al.; "Purification of human respiratory syncytial virus by ultracentrifugation in iodixanol density gradient"; Journal of Virological Methods; Feb. 2008; 147(2-2).
International Preliminary Report dated Jul. 27, 2017 in corresponding International PCT Application No. PCT/US2016/012680, 10 pages.

* cited by examiner

*Primary Examiner* — Janice Li
(74) *Attorney, Agent, or Firm* — Ohlandt, Greeley, Ruggiero & Perle, L.L.P.

(57) ABSTRACT

A method of purifying a viral vector is provided. The method includes loading a nonionic density gradient into a continuous flow centrifuge rotor; loading a material including the viral vector into the continuous flow centrifuge rotor; rotating the continuous flow centrifuge rotor in a manner sufficient to separate the viral vector and a predictable contaminate from the material in the nonionic density gradient; and unloading the separated viral vector and the predicable contaminant from the continuous flow centrifuge rotor.

36 Claims, 31 Drawing Sheets
(16 of 31 Drawing Sheet(s) Filed in Color)

| Fraction | CsCl weight (g/cc) |
|---|---|
| A1 | 1.034 |
| A2 | 1.154 |
| A3 | 1.22 |
| A4 | 1.244 |
| A5 | 1.26 |
| A6 | 1.269 |
| A7 | 1.26 |
| A8 | 1.256 |
| A9 | 1.247 |
| A10 | 1.24 |
| A11 | 1.226 |
| A12 | 1.223 |
| A13 | 1.222 |
| A14 | 1.216 |
| A15 | 1.208 |
| A16 | 1.208 |
| A17 | 1.194 |
| A18 | 1.156 |
| A19 | 1.157 |
| A20 | 1.14 |
| A21 | 1.126 |
| A22 | 1.129 |
| A23 | 1.11 |
| A24 | 1.099 |
| A25 | 1.095 |
| A26 | 1.085 |
| A27 | 1.079 |
| A28 | 1.071 |
| A29 | 1.07 |
| A30 | 1.048 |

| Fraction | CsCl weight (g/cc) |
|---|---|
| B1 | 1.281 |
| B2 | 1.156 |
| B3 | 1.236 |
| B4 | 1.229 |
| B5 | 1.231 |
| B6 | 1.227 |
| B7 | 1.212 |
| B8 | 1.206 |
| B9 | 1.19 |
| B10 | 1.187 |
| B11 | 1.162 |
| B12 | 1.16 |
| B13 | 1.142 |
| B14 | 1.142 |
| B15 | 1.126 |
| B16 | 1.126 |
| B17 | 1.113 |
| B18 | 1.099 |
| B19 | 1.095 |
| B20 | 1.084 |
| B21 | 1.079 |
| B22 | 1.067 |
| B23 | 1.067 |

Iodixanol refractive index and AAV recovery from Lot12-303

| Fraction | Iodixanol % | Refractive index | AAV titer (vg/ml) | Volume (ml) | Total AAV(vg) | |
|---|---|---|---|---|---|---|
| C1 | | 1.3435 | | | | |
| C2 | 27 | 1.3831 | 1.82E+12 | 4 | 7.28E+12 | |
| C3 | 41 | 1.4013 | 9.07E+12 | 4 | 3.63E+12 | |
| C4 | 46 | 1.4096 | 4.55E+13 | 4 | 1.82E+13 | |
| C5 | 48 | 1.4111 | 9.05E+13 | 4 | 3.62E+13 | |
| C6 | 46 | 1.4106 | 1.53E+13 | 4 | 6.12E+13 | |
| C7 | 44 | 1.4066 | 2.20E+13 | 4 | 8.80E+13 | |
| C8 | 42 | 1.4039 | 2.77E+13 | 4 | 1.11E+14 | |
| C9 | 41 | 1.3996 | 2.74E+13 | 4 | 1.10E+14 | |
| C10 | 37 | 1.3939 | 1.98E+13 | 4 | 7.92E+13 | |
| C11 | 33 | 1.3875 | 9.68E+12 | 4 | 3.87E+13 | |
| C12 | 30 | 1.3823 | | | | |
| C13 | 27 | 1.3772 | | | | |
| C14 | 24 | 1.3721 | | | | |
| C15 | 20 | 1.368 | | | | |
| C16 | 18.5 | 1.3643 | | | | |
| C17 | 16 | 1.3605 | | | | |
| C18 | 14.5 | 1.3575 | | | | |
| C19 | 13 | 1.3544 | | | | |
| C20 | 11 | 1.352 | | | | |
| C21 | 10 | 1.3501 | | | | |
| C22 | 8.5 | 1.3482 | | | | |
| C23 | 7 | 1.3469 | | | | |
| C24 | 6.5 | 1.3451 | | | | |
| C25 | 6 | 1.3441 | | | | |
| C26 | 4 | 1.3435 | | | | |
| C27 | | 1.3424 | | | | |
| C28 | | 1.3417 | | | | |
| C29 | | 1.341 | | | | |
| C30 | | 1.3405 | | | | |
| Sample loaded | | | 2.29E+13 | 100 | 2.29E+15 | 100% |
| Flow through | | | 2.97E+12 | 100 | 2.97E+14 | 13% |
| Fraction collected | | | | | 5.42E+14 | 24% |

Iodixanol refractive index and AAV recovery from Experiment D

| Fraction | Iodixanol % | Refractive index | AAV titer (vg/ml) | Volume (ml) | Total AAV(vg) | |
|---|---|---|---|---|---|---|
| D1 | | 1.3411 | | | | |
| D2 | 22 | 1.3756 | 1.04E+11 | 4 | 4.16E+11 | |
| D3 | 36 | 1.3956 | 2.32E+11 | 4 | 9.28E+11 | |
| D4 | 45 | 1.4078 | 1.19E+11 | 4 | 4.76E+11 | |
| D5 | 47 | 1.4108 | 1.45E+11 | 4 | 5.80E+11 | |
| D6 | 47 | 1.4108 | 2.99E+11 | 4 | 1.20E+12 | |
| D7 | 46 | 1.4091 | 7.04E+11 | 4 | 2.82E+12 | |
| D8 | 43 | 1.4058 | 1.75E+12 | 4 | 7.00E+12 | |
| D9 | 41 | 1.4016 | 1.68E+12 | 4 | 6.72E+12 | |
| D10 | 37 | 1.3964 | 7.17E+11 | 4 | 2.87E+12 | |
| D11 | 33 | 1.3905 | 8.22E+11 | 4 | 3.29E+12 | |
| D12 | 29 | 1.3855 | 3.16E+11 | 4 | 1.26E+12 | |
| D13 | 26 | 1.3813 | | | | |
| D14 | 23 | 1.3766 | | | | |
| D15 | 20 | 1.3726 | | | | |
| D16 | 17 | 1.3686 | | | | |
| D17 | 15 | 1.3652 | | | | |
| D18 | 13 | 1.3625 | | | | |
| D19 | 11 | 1.36 | | | | |
| D20 | 9 | 1.3576 | | | | |
| D21 | | 1.3556 | | | | |
| D22 | | 1.3535 | | | | |
| D23 | | 1.3517 | | | | |
| D24 | | 1.35 | | | | |
| D25 | | 1.3483 | | | | |
| D26 | | 1.3465 | | | | |
| D27 | | 1.345 | | | | |
| D28 | | 1.344 | | | | |
| D29 | | 1.343 | | | | |
| D30 | | 1.3426 | | | | |
| Sample loaded | | | 2.09E+12 | 100 | 2.09E+14 | 100% |
| Flow through | | | 3.16E+11 | 100 | 3.16E+13 | 15% |
| Fraction collected | | | | | 2.52E+13 | 12% |

Iodixanol refractive index and AAV recovery from Experiment E in 230-ml rotor

| Fraction | Iodixanol % | Refractive index | AAV titer (vg/ml) | Volume (ml) | Total AAV(vg) | |
|---|---|---|---|---|---|---|
| E1 | 16 | 1.3601 | | 18 | | |
| E2 | 49 | 1.4135 | 1.81E+11 | 8 | 1.45E+12 | |
| E3 | 53 | 1.4205 | 2.02E+11 | 8 | 1.62E+12 | |
| E4 | 52.5 | 1.4192 | 6.53E+11 | 8 | 5.22E+12 | |
| E5 | 51 | 1.4156 | 1.20E+12 | 8 | 9.60E+12 | |
| E6 | 47 | 1.4112 | 3.31E+12 | 8 | 2.65E+13 | |
| E7 | 44 | 1.4064 | 4.95E+12 | 8 | 3.96E+13 | |
| E8 | 41 | 1.4112 | 1.33E+13 | 8 | 1.06E+14 | |
| E9 | 36 | 1.3946 | 2.67E+12 | 8 | 2.14E+13 | |
| E10 | 33 | 1.3864 | 4.50E+11 | 8 | 3.60E+12 | |
| E11 | 29 | 1.3793 | 4.02E+11 | 8 | 3.22E+12 | |
| E12 | 25 | 1.3736 | | 8 | | |
| E13 | 21 | 1.3683 | | 8 | | |
| E14 | 18 | 1.3636 | | 8 | | |
| E15 | 20 | 1.3595 | | 8 | | |
| E16 | 14 | 1.3561 | | 8 | | |
| E17 | 12 | 1.353 | | 8 | | |
| E18 | 10 | 1.3508 | | 8 | | |
| E19 | 9 | 1.3482 | | 8 | | |
| E20 | 7 | 1.3463 | | 8 | | |
| E21 | | 1.3446 | | 8 | | |
| E22 | | 1.3432 | | 8 | | |
| E23 | | 1.3421 | | 8 | | |
| E24 | | 1.3412 | | 8 | | |
| E25 | | 1.3406 | | 8 | | |
| E26 | | 1.3404 | | 8 | | |
| E27 | | 1.3408 | | 8 | | |
| E28 | | 1.3405 | | 8 | | |
| Sample loaded | | | 2.09E+12 | 160 | 3.34E+14 | 100% |
| Flow through | | | 4.54E+11 | 160 | 7.26E+13 | 22% |
| Fraction collected | | | | | 2.03E+14 | 61% |

Iodixanol refractive index and AAV recovery from Experiment G

| Fraction | Iodixanol % | Refractive index | AAV titer (vg/ml) | Volume (ml) | Total (vg) | |
|---|---|---|---|---|---|---|
| G1 | 9 | 1.3458 | | 8 | | |
| G2 | 27 | 1.3821 | 8.50E+10 | 4 | | |
| G3 | 40 | 1.4005 | 1.33E+11 | 4 | 5.32E+11 | |
| G4 | 46 | 1.4088 | 3.08E+11 | 4 | 1.23E+12 | |
| G5 | 47 | 1.4098 | 4.54E+11 | 4 | 1.82E+12 | |
| G6 | 46 | 1.409 | 9.83E+11 | 4 | 3.93E+12 | |
| G7 | 45 | 1.4071 | 8.68E+11 | 4 | 4.47E+12 | |
| G8 | 42 | 1.4032 | 6.34E+11 | 4 | 2.54E+12 | |
| G9 | 39 | 1.3991 | 5.15E+11 | 4 | 2.06E+12 | |
| G10 | 36 | 1.3953 | 4.53E+11 | 4 | 1.81E+12 | |
| G11 | 33 | 1.391 | 4.25E+11 | 4 | 1.70E+12 | |
| G12 | 30 | 1.387 | | 4 | | |
| G13 | 27 | 1.3833 | | 4 | | |
| G14 | 25 | 1.3796 | | 4 | | |
| G15 | 22 | 1.376 | | 4 | | |
| G16 | 20 | 1.3726 | | 4 | | |
| G17 | 17 | 1.3692 | | 4 | | |
| G18 | 15 | 1.3661 | | 4 | | |
| G19 | 13 | 1.3631 | | 4 | | |
| G20 | 11 | 1.3608 | | 4 | | |
| G21 | 10 | 1.3583 | | | | |
| G22 | | 1.3564 | | | | |
| G23 | | 1.3549 | | | | |
| G24 | | 1.3534 | | | | |
| G25 | | 1.3524 | | | | |
| G26 | | 1.351 | | | | |
| G27 | | 1.3505 | | | | |
| G28 | | 1.3498 | | | | |
| G29 | | 1.3488 | | | | |
| G30 | | 1.348 | | | | |
| Sample loaded | | | 8.33E+11 | 42.5 | 3.54E+13 | 100% |
| Flow through | | | 1.24E+11 | 127.5 | 1.58E+13 | 45% |
| Fraction collected | | | | | 1.73E+13 | 49% |

Iodixanol refractive index and AAV recovery from Experiment H

| Fraction | Iodixanol % | Refractive index | AAV titer (vg/ml) | Volume (ml) | Total (vg) | |
|---|---|---|---|---|---|---|
| H1 | 5 | 1.34 | | | | |
| H2 | 17 | 1.3885 | 9.32E+11 | 4 | 3.73E+12 | |
| H3 | 36 | 1.3955 | 1.72E+12 | 4 | 6.88E+12 | |
| H4 | 45.5 | 1.4085 | 1.07E+13 | 4 | 4.28E+13 | |
| H5 | 48 | 1.4115 | 2.16E+13 | 4 | 8.64E+13 | |
| H6 | 46.5 | 1.4108 | 3.03E+13 | 4 | 1.21E+14 | |
| H7 | 45 | 1.4082 | 3.45E+13 | 4 | 1.38E+14 | |
| H8 | 43 | 1.4045 | 2.83E+13 | 4 | 1.13E+14 | |
| H9 | 40 | 1.4003 | 2.35E+13 | 4 | 9.40E+13 | |
| H10 | 37.5 | 1.3941 | 1.44E+13 | 4 | 5.76E+13 | |
| H11 | 35.5 | 1.389 | 8.84E+12 | 4 | 3.54E+13 | |
| H12 | 32 | 1.3851 | | | | |
| H13 | 29 | 1.3851 | | | | |
| H14 | 26 | 1.3813 | | | | |
| H15 | 23 | 1.3778 | | | | |
| H16 | 21 | 1.3745 | | | | |
| H17 | 19 | 1.371 | | | | |
| H18 | 17 | 1.368 | | | | |
| H19 | 15 | 1.365 | | | | |
| H20 | 12 | 1.362 | | | | |
| H21 | 11 | 1.3605 | | | | |
| H22 | 10 | 1.3582 | | | | |
| H23 | 9 | 1.3568 | | | | |
| H24 | | 1.3548 | | | | |
| H25 | | 1.3544 | | | | |
| H26 | | 1.3535 | | | | |
| H27 | | 1.3521 | | | | |
| H28 | | 1.3505 | | | | |
| H29 | | 1.3491 | | | | |
| H30 | | 1.347 | | | | |
| Sample loaded | | | 1.32E+13 | 95 | 1.25E+15 | 100% |
| Flow through | | | 4.17E+12 | 95 | 3.96E+14 | 32% |
| Fraction collected | | | | | 6.89E+14 | 55% |

Iodixanol refractive index and AAV recovery from Experiment I

| Fraction | Iodixanol % | Refractive index | AAV titer (vg/ml) | Volume (ml) | Total (vg) | |
|---|---|---|---|---|---|---|
| 1 | | 1.3434 | | 8 | | |
| 2 | 22 | 1.376 | 1.19E+11 | 4 | 4.76E+11 | |
| 3 | 40 | 1.4 | 1.40E+11 | 4 | 5.60E+11 | |
| 4 | 48 | 1.4122 | 2.80E+11 | 4 | 1.12E+11 | |
| 5 | 51 | 1.4154 | 1.21E+12 | 4 | 4.84E+11 | |
| 6 | 49 | 1.4139 | 1.90E+12 | 4 | 7.60E+11 | |
| 7 | 47 | 1.4105 | 1.68E+12 | 4 | 6.72E+12 | |
| 8 | 44 | 1.406 | 1.39E+12 | 4 | 5.56E+12 | |
| 9 | 40 | 1.4005 | 1.03E+12 | 4 | 4.12E+13 | |
| 10 | 36 | 1.3951 | 7.72E+11 | 4 | 2.69E+13 | |
| 11 | 31 | 1.3903 | 6.38E+11 | 4 | 2.55E+13 | |
| 12 | 28 | 1.3865 | | 4 | | |
| 13 | 27 | 1.3827 | | 4 | | |
| 14 | 25 | 1.379 | | 4 | | |
| 15 | 22 | 1.376 | | 4 | | |
| 16 | 20 | 1.3728 | | 4 | | |
| 17 | 17 | 1.3695 | | 4 | | |
| 18 | 15 | 1.3668 | | 4 | | |
| 19 | 14 | 1.3641 | | 4 | | |
| 20 | 12 | 1.362 | | 4 | | |
| Sample loaded | | | 1.46E+13 | 67 | 9.78E+14 | 100% |
| Flow through | | | 1.03E+11 | 670 | 6.90E+13 | 7% |
| Fraction collected | | | | | 3.52E+13 | 4% |

Iodixanol refractive index and AAV recovery from Experiment J

| Fraction | Iodixanol % | Refractive index | AAV titer (vg/ml) | Volume (ml) | Total (vg) | |
|---|---|---|---|---|---|---|
| J1 | | 1.3401 | | | | |
| J2 | 20 | 1.3721 | 2.25E+11 | 4 | 9.00E+11 | |
| J3 | 38 | 1.3982 | 3.60E+11 | 4 | 1.44E+12 | |
| J4 | 47 | 1.4105 | 1.45E+12 | 4 | 5.80E+12 | |
| J5 | 49 | 1.4139 | 4.54E+12 | 4 | 1.82E+13 | |
| J6 | 49 | 1.4136 | 1.80E+13 | 4 | 5.20E+13 | |
| J7 | 47 | 1.4109 | 1.66E+13 | 4 | 6.64E+13 | |
| J8 | 44 | 1.4061 | 1.22E+13 | 4 | 4.88E+13 | |
| J9 | 41 | 1.4012 | 1.03E+13 | 4 | 4.12E+13 | |
| J10 | 37 | 1.3965 | 8.86E+12 | 4 | 3.43E+13 | |
| J11 | 33 | 1.3914 | 6.21E+12 | 4 | 2.48E+13 | |
| J12 | 30 | 1.3876 | | | | |
| J13 | | 1.3831 | | | | |
| J14 | | 1.379 | | | | |
| J15 | | 1.3749 | | | | |
| J16 | | 1.3715 | | | | |
| J17 | | 1.368 | | | | |
| J18 | | 1.3646 | | | | |
| J19 | | 1.362 | | | | |
| J20 | | 1.3598 | | 8 | | |
| Sample loaded | | | 1.54E+13 | 43 | 6.62E+14 | 100% |
| Flow through | | | 3.72E+11 | 430 | 1.60E+14 | 24% |
| Fraction collected | | | | | 32.87E+14 | 43% |

Iodixanol refractive index and AAV recovery from Experiment K

| Fraction | Iodixanol % | Refractive index | AAV titer (vg/ml) | Volume (ml) | Total (vg) | |
|---|---|---|---|---|---|---|
| K1 | 9 | 1.3401 | | | | |
| K2 | 9 | 1.3721 | 1.02E+12 | 4 | 4.08E+12 | |
| K3 | 30 | 1.3982 | 1.76E+12 | 4 | 7.04E+12 | |
| K4 | 42 | 1.4105 | 5.46E+12 | 4 | 2.18E+13 | |
| K5 | 47 | 1.4139 | 1.53E+13 | 4 | 6.12E+13 | |
| K6 | 48 | 1.4136 | 3.71E+13 | 4 | 1.48E+14 | |
| K7 | 46 | 1.4109 | 4.55E+13 | 4 | 1.82E+14 | |
| K8 | 44 | 1.4061 | 3.75E+13 | 4 | 1.50E+14 | |
| K9 | 41 | 1.4012 | 2.82E+13 | 4 | 1.13E+14 | |
| K10 | 38 | 1.3965 | 1.36E+13 | 4 | 5.44E+13 | |
| K11 | 35 | 1.3914 | 1.19E+13 | 4 | 4.76E+13 | |
| K12 | 32 | 1.3876 | | | | |
| K13 | 29 | 1.3831 | | | | |
| K14 | 26 | 1.379 | | | | |
| K15 | 23 | 1.3749 | | | | |
| K16 | 21 | 1.3715 | | | | |
| K17 | 19 | 1.368 | | | | |
| K18 | 17 | 1.3646 | | | | |
| K19 | 15 | 1.362 | | | | |
| K20 | 13 | 1.3598 | | 8 | | |
| Sample loaded | | | 1.66E+13 | 100 | 1.66E+15 | 100% |
| Flow through | | | 4.78E+12 | 100 | 4.78E+14 | 29% |
| Fraction collected | | | | | 7.78E+14 | 47% |

Iodixanol refractive index and AAV recovery from Lot15-219

| Fraction | Iodixanol % | Refractive index | AAV titer (vg/ml) | Volume (ml) | Total (vg) | |
|---|---|---|---|---|---|---|
| L1 | | 1.3341 | | 5 | | |
| L2 | 5 | 1.3426 | | 5 | 0.00E+00 | |
| L3 | 36 | 1.3913 | 4.62E+12 | 5 | 2.31E+13 | |
| L4 | 48 | 1.4119 | 1.35E+12 | 5 | 6.75E+13 | |
| L5 | 43 | 1.4054 | 1.13E+13 | 5 | 5.65E+13 | |
| L6 | 40 | 1.3985 | 6.19E+12 | 5 | 3.10E+13 | |
| L7 | 37 | 1.3939 | 5.29E+12 | 5 | 2.65E+13 | |
| L8 | 36 | 1.3911 | 2.89E+12 | 5 | 1.45E+13 | |
| L9 | 33 | 1.387 | 1.92E+12 | 5 | 9.60E+12 | |
| L10 | 31 | 1.3842 | 2.44E+12 | 5 | 1.22E+13 | |
| L11 | 29 | 1.381 | 1.33E+12 | 5 | 6.65E+12 | |
| L12 | 25 | 1.3746 | 9.66E+11 | 5 | 4.83E+12 | |
| L13 | 20 | 1.37 | | 5 | | |
| L14 | 18 | 1.3665 | | 5 | | |
| L15 | 18 | 1.3635 | | 5 | | |
| L16 | 17 | 1.3609 | | 5 | | |
| L17 | 15 | 1.3586 | | 5 | | |
| L18 | | 1.3566 | | 5 | | |
| L19 | | 1.3554 | | 5 | | |
| L20 | | 1.354 | | 5 | | |
| Sample loaded | | | 6.26E+12 | 100 | 6.26E+14 | 100% |
| FT1 | | | 2.36E+12 | 20 | 4.72E+13 | 8% |
| FT2 | | | 5.34E+12 | 20 | 1.07E+14 | 17% |
| FT3 | | | 1.10E+13 | 20 | 2.20E+14 | 35% |
| FT4 | | | 6.51E+12 | 20 | 1.30E+14 | 21% |
| FT5 | | | 2.85E+12 | 20 | 5.70E+13 | 9% |
| Wash Thru1 | | | 7.75E+11 | 20 | 1.55E+13 | 2% |
| Wash Thru 2 | | | 4.01E+11 | 20 | 8.02E+12 | 1% |
| FT & WT | | | | | 5.85E+14 | 93% |
| Fractions Collected | | | | | 2.24E+14 | 36% |

Iodixanol refractive index and AAV recovery from Lot15-219

| Fraction | Iodixanol % | Refractive index | AAV titer (vg/ml) | Volume (ml) | Total (vg) | |
|---|---|---|---|---|---|---|
| M1 | | 1.333 | | 5 | | |
| M2 | 19 | 1.3716 | 2.19E+11 | 5 | 0.00E+00 | |
| M3 | 41 | 1.4015 | 3.59E+11 | 5 | 1.10E+12 | |
| M4 | 45 | 1.4071 | 1.90E+12 | 5 | 1.80E+12 | |
| M5 | 45 | 1.4084 | 8.89E+12 | 5 | 9.50E+12 | |
| M6 | 44 | 1.406 | 1.05E+13 | 5 | 4.45E+13 | |
| M7 | 43 | 1.4044 | 1.62E+13 | 5 | 5.25E+13 | |
| M8 | 42 | 1.403 | 1.60E+13 | 5 | 8.10E+13 | |
| M9 | 40 | 1.401 | 1.10E+13 | 5 | 8.00E+13 | |
| M10 | 38 | 1.3986 | 8.15E+13 | 5 | 5.50E+13 | |
| M11 | 36 | 1.3957 | 4.41E+12 | 5 | 4.08E+13 | |
| M12 | 34 | 1.3925 | 2.71E+12 | 5 | 2.21E+13 | |
| M13 | 32 | 1.3889 | 2.71E+12 | 5 | 1.36E+13 | |
| M14 | 29 | 1.3859 | 1.97E+12 | 5 | 9.85E+12 | |
| M15 | 27 | 1.3824 | 1.25E+12 | 5 | 6.25E+12 | |
| M16 | | 1.3783 | | 5 | | |
| M17 | | 1.3753 | | 5 | | |
| M18 | | 1.3724 | | 5 | | |
| M19 | | 1.3704 | | 5 | | |
| M20 | | 1.3686 | | 5 | | |
| Sample loaded | | | 1.39E+13 | 140 | 1.95E+15 | 100% |
| FT | | | 8.59E+12 | 140 | 1.20E+15 | 62% |
| Fraction collected | | | | | 4.15E+14 | 21% |

Iodixanol refractive index and AAV recovery from Lot15-299

| Fraction | Iodixanol % | Refractive index | AAV titer (vg/ml) | Volume (ml) | Total (vg) | |
|---|---|---|---|---|---|---|
| N1 | | (-) | | 5 | | |
| N2 | 7 | 1.3326 | | 5 | 0.00E+00 | |
| N3 | 9 | 1.3541 | | 5 | 0.00E+00 | |
| N4 | 32 | 1.3714 | 1.03E+11 | 5 | 5.15E+11 | |
| N5 | 37 | 1.3901 | 3.49E+11 | 5 | 1.75E+12 | |
| N6 | 39 | 1.3976 | 1.33E+12 | 5 | 6.65E+12 | |
| N7 | 38 | 1.3994 | 5.23E+12 | 5 | 2.62E+13 | |
| N8 | 37 | 1.3984 | 4.24E+12 | 5 | 2.12E+13 | |
| N9 | 36 | 1.3968 | 3.44E+12 | 5 | 1.72E+13 | |
| N10 | 35 | 1.3855 | 2.82E+12 | 5 | 1.41E+13 | |
| N11 | 33 | 1.3936 | 1.96E+12 | 5 | 9.80E+12 | |
| N12 | 31 | 1.3901 | 1.07E+12 | 5 | 5.35E+12 | |
| N13 | 29 | 1.3874 | 9.32E+11 | 5 | 4.66E+12 | |
| N14 | 27 | 1.3846 | 4.96E+11 | 5 | 2.48E+12 | |
| N15 | 25 | 1.3819 | 3.11E+11 | 5 | 1.56E+12 | |
| N16 | | 1.379 | | 5 | | |
| N17 | | 1.3764 | | 5 | | |
| N18 | | 1.3735 | | 5 | | |
| N19 | | 1.3711 | | 5 | | |
| N20 | | 1.3693 | | 5 | | |
| Sample loaded | | 140 | 3.31E+12 | 140 | 4.63E+14 | 100% |
| FT | | 140 | 1.28E+12 | 140 | 1.79E+14 | 39% |
| Fraction collected | | | | | 1.11E+14 | 24% |

FIG. 31

METHODS OF PURIFYING ADENO-ASSOCIATED VIRUS (AAV) AND/OR RECOMBINANT ADENO-ASSOCIATED VIRUS (RAAV) AND GRADIENTS AND FLOW-THROUGH BUFFERS THEREFORE

CROSS REFERENCE TO RELATED APPLICATION

This application claims the benefit of U.S. Ser. No. 62/102,645 filed on Jan. 13, 2015, the benefit of U.S. Ser. No. 62/102,650 filed on Jan. 13, 2015, and the benefit of U.S. Ser. No. 62/139,242 filed on Mar. 27, 2015, the entire contents of each of which are incorporated by reference herein.

BACKGROUND

1. Field of the Disclosure

The present disclosure is related to methods of purifying viral vectors such as adeno-associated virus (AAV) and/or recombinant adeno-associated virus (rAAV). More particularly, the present disclosure is related to methods of purification of AAV and/or rAAV using continuous flow centrifugation in a non-ionic density gradient and, preferably, in a single purification step. The present disclosure is also related to density gradients and flow through buffers for such continuous flow centrifugation methods.

2. Description of Related Art

Viral vectors are used to deliver genetic material into host cells for various gene therapy applications. During such gene therapy applications, the delivery of the genetic materials into the host cells uses the viral vector to carry therapeutic genes into a human cell.

Viral vectors are formed by modifying one or more viruses to deliver a desired genetic material into the host cell. For example, some viral vectors are formed by replacing the disease causing genes in a virus with genes that provide a desired effect in the host cell. The replacing of genes in the virus can be performed so that the viral vector retains its ability to infect and replicate.

As a result, the formation of viral vectors has more recently been focused on viruses that are known to infect the target species without causing any known disease. Stated another way, the formation of viral vectors has more recently been focused on non-pathogenic viruses. Viruses that have been the focus of much study for use in the development of viral vectors are adeno-associated virus (AAV) and/or recombinant adeno-associated virus (rAAV). To that end, a number of gene therapy pharmaceuticals using AAV and/or rAAV are in various stages of development, clinical trial, and/or human trial.

Current purification technologies and techniques available can deliver viral vectors of the required purity through the use of multiple purification techniques. These typically employ analytical batch centrifugation technique (e.g., tube rotor centrifugation) and/or chromatography techniques. When the batch centrifugation method employs a tube rotor, multiple runs of this separation step are necessary to process an entire batch/lot of product. These separate runs are pooled together to provide a desired volume of purified viral vector. The batch centrifugation processes may be considered a bottle neck in research, development, manufacturing, scale up, product optimization, and other uses of viral vectors. Thus, batch centrifugation may not be considered to be rapid enough and/or to be cost effective enough for certain uses.

It is believed the present disclosure that there is a continuing need for methods of purifying AAV and/or rAAV consistently in larger volumes efficiently and at lower costs than previously possible.

SUMMARY

Methods of purifying AAV and/or rAAV using a continuous flow centrifuge are provided. The continuous flow centrifugation methods of the present disclosure purify AAV and/or rAAV in a single purification step. The purification disclosed herein is not merely a concentration of AAV and/or rAAV, but rather a removal of contaminants such as, but not limited to, proteins, DNA, carbohydrates, and others that are not of interest.

In some embodiments, the single centrifugation step methods of the present disclosure purify AAV and/or rAAV in quantities sufficient for research, development, manufacturing, scale up, product optimization, and other uses of viral vectors.

In some embodiments, the methods make use of a non-ionic density gradient.

The nonionic density gradient can be selected from the group consisting of a gradient commercially available under the tradename Percoll®, a gradient of 5-(N-2,3-dihydroxypropylacetamido) 2,4,6-tri-iodo-N—N'-bis(2,3-dihydroxypropyl)isophthalamide that is commercially available under the tradenames Accudenz®, Histodenz™, and Nycodenz® (referred to herein as "iohexol"), a gradient of 5,5'-[(2-hydroxy-1,3-propanediyl)-bis (acetylimino)]bis-[N,N bis (2,3dihydroxypropyl)-2,4,6-triiodobenzenedicarboxamide that is commercially available under the tradenames OptiPrep® and Visipaque® (referred to herein as "iodixanol"), a gradient of 2-({3-(acetylamino)-5-[acetyl(methyl) amino]-2,4,6-triiodobenzoyl}amino)-2-deoxy-D-glucopyranose that is commercially available under the tradename Amipaque® (referred to herein as "metrizamide"), any combinations thereof.

The nonionic density gradient material can be modified or unmodified iodixanol in an aqueous buffer solution.

In some embodiments using unmodified nonionic density gradient material in an aqueous buffer solution, the present disclosure provides a continuous flow centrifugation process that can purify AAV and/or rAAV with a predictable contaminant present. As used herein, the term "predictable contaminant" shall mean a contaminant that co-purifies with and/or purifies in proportion to the viral vector of interest (the "target vector"). In some instances, the predictable contaminant may be bound to the target vector. The predictable contaminant can be one or more contaminants detected using SDS-PAGE as a single band such as at about 40 kilo Daltons (kDa) or can be multiple contaminants detected as multiple bands (e.g., 15-45 kDa).

In some embodiments using modified nonionic density gradient material in an aqueous buffer solution, the term "modified" shall mean that the nonionic density gradient material includes one or more modifying agents not selected to be contributing to the density of the gradient specifically such as a buffer, pH adjustor or other components e.g., surfactant layer, a solubilizing agent, a stabilising agent, ionic or anionic surfactants, ionic or anionic detergents, ionic or anionic salts, and any combinations thereof. Moreover, the term "modified" shall mean that the nonionic density gradient material includes the modifying agent(s), and/or that the flow through buffer in use with the nonionic density gradient material includes the modifying agent(s), and/or that the material or lysate carrying the target vector includes the modifying agent(s), and any combinations thereof.

As used here, the concept of materials being selected as modifiers where these materials are not intended to contribute to the density of the gradient means that the material will not specifically change the shape of the gradient or the overall slope of the gradient to generate a desired gradient shape. For example, a 20% w/v solution of CsCl has a density of 1.149 g/cm$^3$, whereas the expected isopycnic banding concentration of AAV and/or rAAV is understood to be 1.38 g/cm$^3$. Thus, concentrations of CsCl up to about 40% w/v can be added to the gradient as a modifier without affecting the density of the gradient material within the meaning of the present application.

While certain materials may be considered to be density gradient media, it is recognized by the present disclosure that those same media have other benefits to the purification process. These modifiers can have a density gradient function in typical applications, but the addition to the gradient in the amounts specified by the present application is for the purpose of a gradient modifier—that alters the relationship between the predictable contaminant and the target vector. For example, it is believed that CsCl and/or NaCl can provide sufficient ionizing potential to the density gradient, which can alter the co-purification interaction of protein:protein, protein:DNA, protein:carbohydrate, and other relationships, but without necessarily changing the density of the gradient.

The purification methods disclosed herein—even when using the unmodified gradients—do not require the pooling of multiple continuous flow centrifugation steps or multiple tube rotor runs. Rather, the methods of the present disclosure provide for a single step, single density gradient continuous flow centrifugation process to purify AAV and/or rAAV— with a predictable contaminant or without a predictable contaminant.

In a particularly preferred embodiment, the density gradient is a modified iodixanol gradient of a maximum density 50% w/v of iodixanol in an aqueous buffer solution. In some embodiments, the gradient is modified with ionic salts in the form of one or more of caesium chloride (CsCl), potassium chloride (KCl), sodium chloride (NaCl), and any combinations thereof.

A method of purifying a viral vector is provided. The method includes loading a nonionic density gradient into a continuous flow centrifuge rotor; loading a material including the viral vector into the continuous flow centrifuge rotor; rotating the continuous flow centrifuge rotor in a manner sufficient to separate the viral vector and a predictable contaminate from the material in the nonionic density gradient; and unloading the separated viral vector and the predicable contaminant from the continuous flow centrifuge rotor.

In some embodiments alone or in combination with the afore or aft mentioned embodiments, the material is a lysate including the viral vector.

In some embodiments alone or in combination with the afore or aft mentioned embodiments, the nonionic density gradient is iodixanol in a solution with an aqueous buffer.

In some embodiments alone or in combination with the afore or aft mentioned embodiments, the aqueous buffer is phosphate-buffered saline (PBS).

In some embodiments alone or in combination with the afore or aft mentioned embodiments, the nonionic density gradient is iodixanol in a solution of between 1 and 60 percent weight per volume (% w/v) with an aqueous buffer.

In some embodiments alone or in combination with the afore or aft mentioned embodiments, the nonionic density gradient is iodixanol in a solution of between 25 and 50% w/v with an aqueous buffer.

In some embodiments alone or in combination with the afore or aft mentioned embodiments, the iodixanol is a two-layered stepped gradient having a 25% w/v layer and a 50% w/v layer.

In some embodiments alone or in combination with the afore or aft mentioned embodiments, the separated viral vector includes at least 47% and, in some embodiments, up to 65%, of the viral vector in the material.

In some embodiments alone or in combination with the afore or aft mentioned embodiments, the step of rotating the continuous flow centrifuge rotor further includes rotating in the presence of a modifying agent that is sufficient to remove the predicable contaminant from the material. The modifying agent can be included in one or more of the nonionic gradient, a flow through buffer, and the material.

In some embodiments alone or in combination with the afore or aft mentioned embodiments, the modifying agent is selected from the group consisting of caesium chloride (CsCl), potassium chloride (KCl), sodium chloride (NaCl), Nycodenz, Sucrose, Glycerol, Glucose, potassium Bromide (KBr), and any combinations thereof. In embodiments where the modifying agent is CsCl, the CsCl can be present at a concentration of up to 40% w/v, more preferably at a concentration of 20% w/v, and any subranges there between.

In some embodiments alone or in combination with the afore or aft mentioned embodiments, the separated viral vector includes at least 21% of the viral vector in the material.

In some embodiments alone or in combination with the afore or aft mentioned embodiments, the viral vector is at least one of adeno-associated virus (AAV) and recombinant adeno-associated virus (rAAV).

In some embodiments alone or in combination with the afore or aft mentioned embodiments, the step of loading the nonionic density gradient into the continuous flow centrifuge rotor includes one or more of a static gradient loading or a dynamic gradient loading, a static gradient unloading or a dynamic gradient unloading, a step of orienting the nonionic density gradient, and loading a mixed gradient or a linear gradient.

In some embodiments alone or in combination with the afore or aft mentioned embodiments, the method further includes the step of performing a second centrifugation step to remove the predictable contaminant from the separated viral vector. The second centrifugation step can be a continuous or non-continuous centrifugation. The second centrifugation step can include using a gradient with an ionic modifying agent sufficient to remove the predicable contaminate.

A method of purifying a viral vector is also provided that includes loading a nonionic density gradient into a continuous flow centrifuge rotor; loading a material including the viral vector into the continuous flow centrifuge rotor, rotating the continuous flow centrifuge rotor in a manner sufficient to separate the viral vector from the material in the nonionic density gradient; and unloading the separated viral vector from the continuous flow centrifuge rotor. In this embodiment, the viral vector is at least one of AAV and rAAV.

In some embodiments alone or in combination with the afore or aft mentioned embodiments, the step of rotating the continuous flow centrifuge rotor further includes rotating in the presence of a modifying agent that is sufficient to remove predicable contaminants from the material.

In some embodiments alone or in combination with the afore or aft mentioned embodiments, the nonionic density gradient includes a modifying agent that is sufficient to remove predicable contaminants from the material.

In some embodiments alone or in combination with the afore or aft mentioned embodiments, the step of rotating the continuous flow centrifuge rotor further includes rotating while using a flow through buffer, the flow through buffer includes a modifying agent that is sufficient to remove predicable contaminants from the material.

In some embodiments alone or in combination with the afore or aft mentioned embodiments, the material includes a modifying agent that is sufficient to remove predicable contaminants from the material.

In the afore mentioned embodiments including the modifying agent, the modifying agent can be CsCl at a concentration of up to 40% w/v.

A method of purifying a viral vector further provided that includes loading a nonionic density gradient into a continuous flow centrifuge rotor, the nonionic density gradient includes iodixanol in a solution of between 25 and 50% w/v and PBS; loading a material including the viral vector into the continuous flow centrifuge rotor, wherein the viral vector is at least one of AAV and rAAV; rotating the continuous flow centrifuge rotor in the presence of CsCl at a concentration of up to 40% w/v in a manner sufficient to separate the viral vector from the material in the nonionic density gradient; and unloading the separated viral vector from the continuous flow centrifuge rotor, wherein the separated viral vector includes at least 21% of the viral vector in the material.

In some embodiments alone or in combination with the afore or aft mentioned embodiments, the nonionic density gradient includes the CsCl.

In some embodiments alone or in combination with the afore or aft mentioned embodiments, the step of rotating the continuous flow centrifuge rotor further includes rotating while using a flow through buffer, the flow through buffer includes the CsCl.

In some embodiments alone or in combination with the afore or aft mentioned embodiments, the material includes the CsCl.

A method of purifying a viral vector also provided that includes loading a nonionic density gradient into a continuous flow centrifuge rotor, the nonionic density gradient includes iodixanol in a solution of between 25 and 50% w/v with PBS; loading a material including the viral vector into the continuous flow centrifuge rotor, wherein the viral vector is at least one of AAV and rAAV; rotating the continuous flow centrifuge rotor in a manner sufficient to separate the viral vector and a predictable contaminant from the material in the nonionic density gradient; and unloading the separated viral vector from the continuous flow centrifuge rotor. The separated viral vector includes at least 47% and, in some embodiments, up to 65%, of the viral vector in the material.

A density gradient for continuous flow centrifugation is provided. The gradient includes iodixanol in an amount selected from the group consisting of 25 and 50% w/v; CsCl in an amount up to 40% w/v; and an aqueous buffer.

In some embodiments alone or in combination with the afore or aft mentioned embodiments, the gradient further includes 100 mM sodium citrate.

In some embodiments alone or in combination with the afore or aft mentioned embodiments, the aqueous buffer includes PBS.

In some embodiments alone or in combination with the afore or aft mentioned embodiments, the amount of iodixanol can be 25% w/v and/or 50% w/v.

In some embodiments alone or in combination with the afore or aft mentioned embodiments, the amount of CsCl can be 20% w/v.

A flow through buffer for continuous flow centrifugation is provided that includes aqueous buffer, sodium citrate, and CsCl.

In some embodiments alone or in combination with the afore or aft mentioned embodiments, the sodium citrate is 100 mM sodium citrate.

In some embodiments alone or in combination with the afore or aft mentioned embodiments, aqueous buffer includes PBS.

In some embodiments alone or in combination with the afore or aft mentioned embodiments, the CsCl can be present in an amount up to 40% w/v or in an amount of 20% w/v.

The above-described and other features and advantages of the present disclosure will be appreciated and understood by those skilled in the art from the following detailed description, drawings, and appended claims.

BRIEF DESCRIPTION OF THE DRAWINGS

This application contains at least one drawing executed in color. Copies of this patent or patent application publication with color drawing(s) will be provided by the Office upon request and payment of the necessary fee.

FIG. 31 is a table that compares the Experiments C, D, H, K, L, M, E, G, I and J.

DETAILED DESCRIPTION

Figure 1:
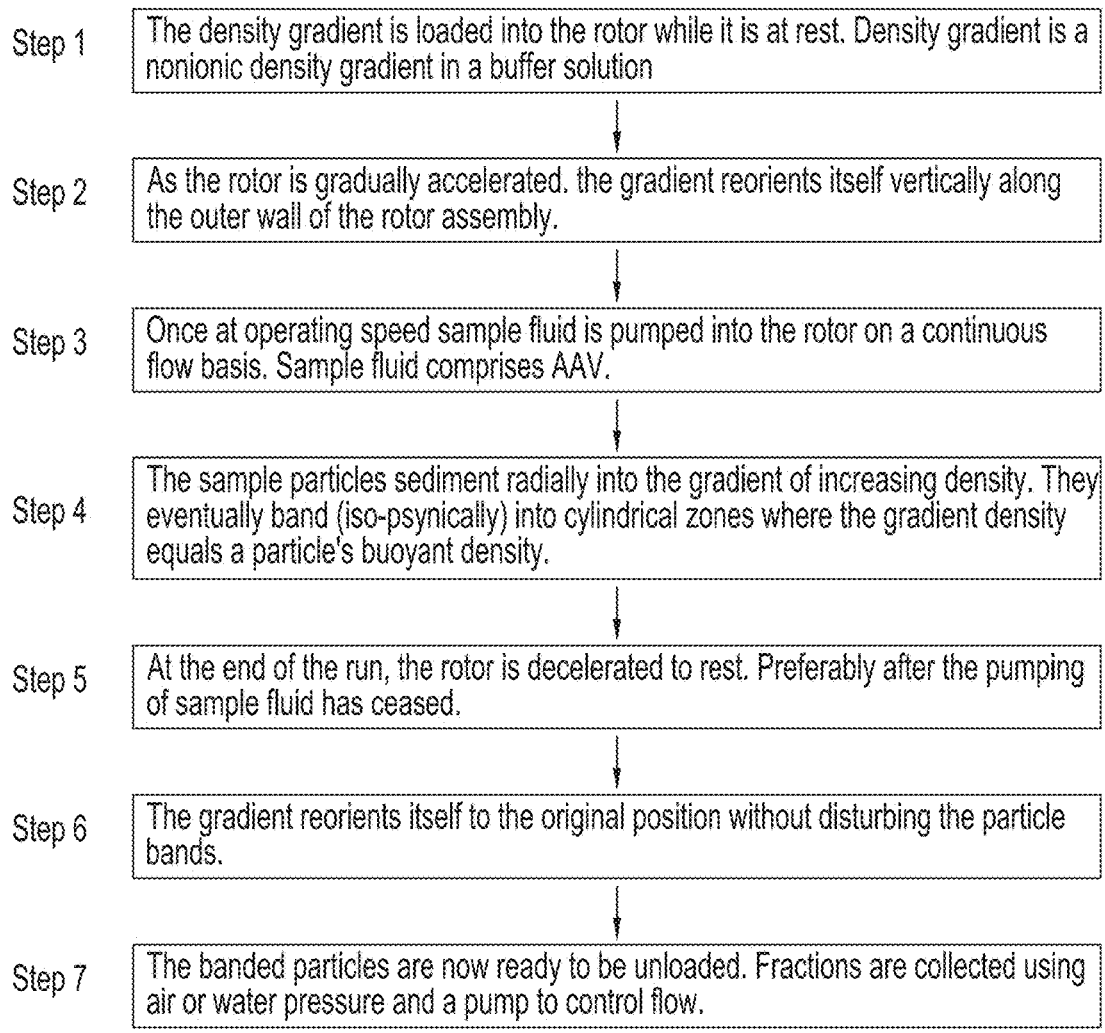
FIG. 1 is a flow chart of an exemplary embodiment of a purification method according to the present disclosure.
Figure 2:
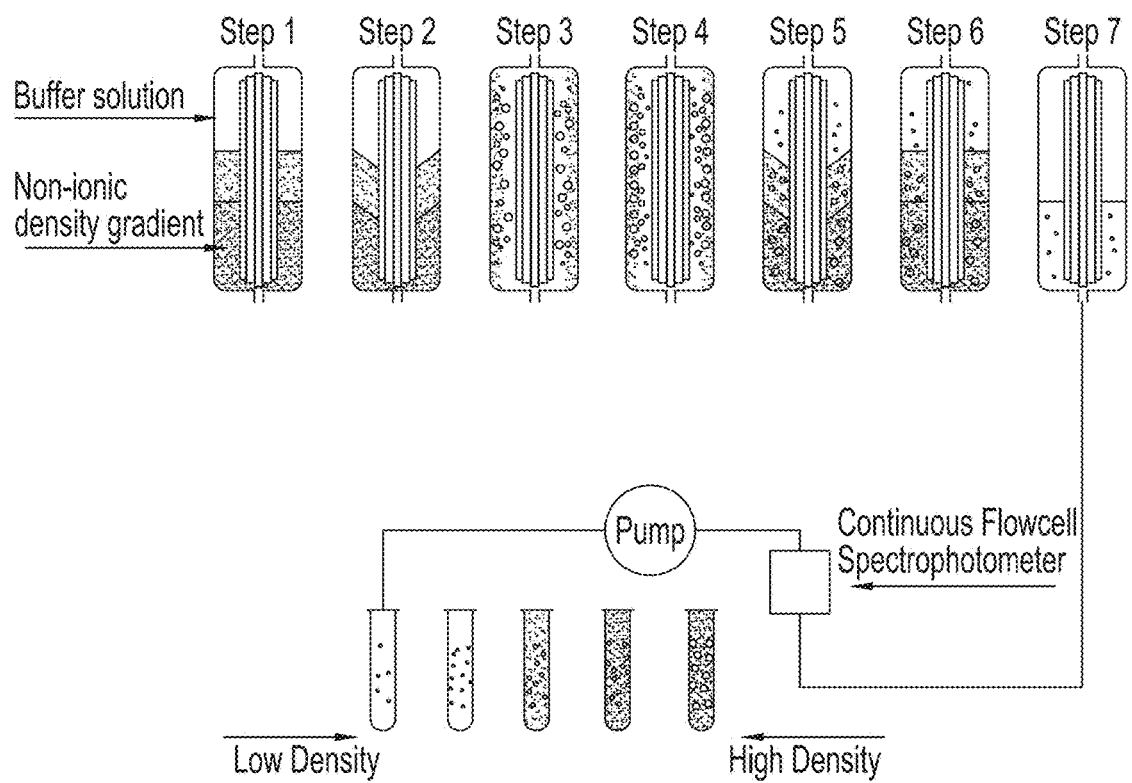
FIG. 2 is a schematic depiction of the purification method of FIG. 1.

Referring to the drawings and in particular to FIGS. 1 and 2, an exemplary embodiment of a purification method according to the present disclosure is shown. The method of the present disclosure uses continuous flow centrifugation to purify AAV and/or rAAV. However, it is also contemplated by the present disclosure for the method to not be affected by the serotype used, and therefore can be applied to a range of AAV, rAAV, or any other vector types.

As used herein, the term continuous flow centrifugation shall generally mean to continuously pass the sample fluid or material (hereinafter "material") to be separated—namely a material containing a target vector such as AAV and/or rAAV and one or more contaminants—through a rotor containing a density gradient maintained within the rotor during high speed operation. At the end of this continuous flow of material through the rotor, the rotor can be stopped and the purified target vector captured in the density gradient can be removed from the rotor. Such "continuous flow centrifugation" is also often referred to zonal or sector centrifugation or ultracentrifugation. Suitable centrifugation devices include the AW Promatix 1000™, the AW PKII, and the AW KII, which are commercially available from the Applicant of the present disclosure.

Thus, the continuous flow centrifugation process of the present disclosure can process tens of liters of material per hour or more—which is in stark contrast to the batch or tube centrifugation techniques of the prior art.

Without wishing to be bound by any particular theory, AAV and/or rAAV are known to have a small size—such as about 20 nanometers (nm)—a size that is believed by the present disclosure to make continuous flow centrifugation difficult as compared to analytical batch centrifugation techniques. Due to the small genome of AAV (i.e., 4.8 kilobase) only small genes can be coded into the AAV. Without wishing to be bound by any particularly theory, this small size is believed to mean that any changes to the structure of AAV caused by gene inserts, converting the AAV to rAAV, would be small enough to not alter the purification. Thus, it is believed that AAV would purify in a manner consistent with the purification of rAAV. Additionally, the converse is also believed by the present disclosure to be true, namely that rAAV is believed to purify in a manner consistent with the purification of AAV.

The method of the present disclosure provides a density gradient that remains stable at the speeds and conditions of continuous flow centrifugation, yet is of a sufficient density range to allow for purification of AAV and/or rAAV in a single step with a predictable contaminant or without a predictable contaminant.

Referring again to FIGS. 1 and 2, an exemplary method according to the present disclosure includes a first or gradient loading step, a second or gradient orientation step, a third or material flow step, a fourth or target vector banding step, a fifth or rotor deceleration step, a sixth or gradient re-orientation step, and a seventh or banded target vector unloading step.

It should be recognized that the continuous flow centrifugation method of FIGS. 1 and 2 is described by way of example as a method that includes, for example, static gradient loading, static gradient unloading, and loading of an unmixed (e.g., discontinuous) or layered (e.g., step) gradient. It is also contemplated for the continuous flow centrifugation method of the present disclosure to include any continuous flow method steps such as, but not limited to, dynamic gradient loading, dynamic gradient unloading, loading of mixed or linear (e.g., continuous) gradients, and any combinations thereof.

During the first or gradient loading step, a nonionic density gradient and a buffer solution are pumped into the centrifuge rotor. The rotor can have any desired configuration such as, but not limited to, K3 rotors commercially available from the Applicant of the present disclosure, as well as one or more of K6, K10, PK3, PK3-400, PK3-800, PK6, PK10, PX-55 ml, PX-120 ml, PX-230 ml, and others.

The nonionic density gradient can be any nonionic density gradient such as, but not limited to, Percoll®, iohexol, iodixanol, metrizamide, and any combinations thereof. In one preferred embodiment, the nonionic density gradient is iodixanol. The density gradient in this embodiment includes iodixanol in a solution of between 1 and 60 percent weight per volume (% w/v) with an aqueous buffer, with between 25 and 50% w/v being preferred, and with a maximum density of 50% w/v being most preferred.

In other embodiments alone or in combination with one or more of the aforementioned or aft mentioned embodiments, the nonionic density gradient is a modified iodixanol density gradient. Here, the nonionic density gradient can include a modifying agent.

In some embodiments, the modifying agent is in the form of an ionic modifier such as, but not limited to, salts in the form of one or more of caesium chloride (CsCl), potassium chloride (KCl), sodium chloride (NaCl), and any combinations thereof. The concentration of the ionic modifying agent can be between 20 mM and 5M.

In other embodiments alone or in combination with one or more of the aforementioned or aft mentioned embodiments, the nonionic density gradient can include modifying agents in the form of ionic or anionic surfactants and/or detergents such as, but not limited, to polysorbate, commercially available as Tween®, Cetyl trimethylammonium bromide (CTAB), Cetyltrimethylammonium chloride (CTAC), CHAPS (3-[(3-Cholamidopropyl)dimethylammonio]-1-propanesulfonate), NP-40 Tergitol-type NP-40, and Triton® at concentrations between 0.05% w/v and 7% w/v.

In other embodiments alone or in combination with one or more of the aforementioned or aft mentioned embodiments, the nonionic density gradient can include other modifying agents such as, but not limited to Percoll®, iohexol, metrizamide Sucrose, Glycerol, Glucose, potassium bromide (KBr), caesium chloride (CsCl), and any combinations thereof in a percentage of the total up to 40% w/v or as a concentration e.g., up to 2M.

In a particularly preferred embodiment, the density gradient is a modified iodixanol gradient of 25% and 50% w/v in an aqueous buffer solution modified with CsCl.

During the second or gradient orientation step, the rotor is rotated at gradually increasing speeds sufficient to orient the nonionic density gradient and buffer solution from the horizontal orientation from the first step to a vertical orientation in which the nonionic density gradient having a higher density is proximate to the outer wall of the rotor while the buffer solution having a lower density is proximate to the center of rotation of the rotor.

Stated another way, the method of the present disclosure loads the nonionic density gradient in a discontinuous manner in the first step, but upon acceleration the density gradient becomes linearized or continuous; effectively the steps merge and a continuous gradient is formed. In certain situations, the linearization of the gradient may occur at the beginning of the acceleration phase, the product flow phase or may occur during the product loading or not occur until the braking phase of operation. Typically, linearization occurs once the operational maximum/set speed is reached.

Once the density gradient is oriented, during a slow acceleration phase to about 3,500 rpm (i.e., about 1,000×g) or thereabouts, a maximum acceleration of the rotor begins to a predetermined speed sufficient for purification, the material that has the AAV and/or rAAV suspended therein is pumped into the rotor during the third or material flow step. The material is continuously pumped through the rotor during the third or material flow step. During the fourth step, flow through buffer is circulated through the density gradient while the target vector is banded, with the target vector (i.e., AAV and/or rAAV) sedimenting radially into the gradient and banding isopycnically in a zone where the density of the gradient approximates or equals the target vector's buoyant density. The flow through buffer passes through and exits the rotor as new buffer is pumped into the rotor.

In one exemplary embodiment where the density gradient is iodixanol at a maximum density of 60% w/v and the material includes AAV and/or rAAV, the AAV and/or rAAV bands at between 32 to 48% w/v, more typically at 35 to 47% w/v. Here, it is contemplated by the present disclosure for the material to be pumped at a flow rate of between 5 milliliters per min (mL/min) and 100 mL/min and the rotor to have a volume of between 120 mL and 3.2 L or more. Preferably, the rotor and process are scalable—between these volumes—meaning that the target vector bands at the same density location in the density gradient and that the density gradient essentially has the same separation range and capacity at each scale of operation, by having the same characteristics of, at a minimum, shape of the gradient curve and density range regardless of the size of the rotor and/or the flow rate of the material pumped through the rotor.

At a predetermined point such as when it has been determined that the density gradient is loaded with material to a desired amount, the loading of material is stopped and the flow through buffer is continuously loaded during the fourth or banding step. Next, the rotor speed is reduced during the fifth or rotor deceleration step in a rapid phase followed by a slower phase to allow for reorientation of the density gradient prior to reaching a stopped or rest position. During the sixth step, the slower deceleration end phase, the density gradient will reorient to the original position without disturbing the bands of the AAV and/or rAAV captured in the density gradient.

Finally, the banded AAV and/or rAAV can be unloaded from the continuous flow centrifuge rotor during the seventh or banded target vector unloading step in a known manner.

Without wishing to be bound to any particular theory, it is believed that the gradients (density or otherwise) used in small scale batch or tube centrifugation processes for AAV and/or rAAV—such as CsCl—although having the required density range lack the stability determined by the present disclosure as being necessary for AAV and/or rAAV purification. The density gradients of the present disclosure such as iodixanol—in the disclosed concentrations—have proven to have both the necessary stability and density for AAV and/or rAAV purification in a single step.

In some embodiments, it has been determined by the present disclosure that purification of the AAV and/or rAAV in the iodixanol density gradient may result in a predictable contaminant also being captured at the preferred banding density range of the AAV and/or rAAV.

In some embodiments and depending on the end use of the purification of the AAV and/or rAAV, the predictable contaminant may be within acceptable parameters depending on the final use of the purified AAV and/or rAAV.

In other embodiments and depending on the end use of the purification of the AAV and/or rAAV, the predictable contaminant may not be within the acceptable parameters, but can be removed in one or more subsequent purification steps—including but not limited to tube rotor centrifugation, dialysis purification, chromatography purification, and/or continuous flow centrifugation.

In still other embodiments and depending on the end use of the purification of the AAV and/or rAAV, it is contemplated by the present disclosure for the predictable contaminant to be removed by the single step continuous flow centrifugation in the iodixanol density gradient. For example, it has been determined that the predictable contaminant can be removed (i.e., captured at a different position from the AAV and/or rAAV in the iodixanol density gradient and/or in the buffer solution) using one or more of the modified gradients discussed herein. Thus, it has been determined by the present disclosure that using only the modified nonionic density gradients disclosed herein, the disclosed method can provide a single step continuous flow centrifugation to purify AAV and/or rAAV.

The purification disclosed herein is not merely a concentration of vectors, but rather a removal of contaminants that are not of interest in the purification scheme. In some embodiments, the methods of the present disclosure provide a purity of AAV and/or rAAV that is the same or better than that provided by small scale batch or tube centrifugation purification employing multiple CsCl gradients.

Additionally, the purification disclosed herein—even when using the modified gradients—does not require multiple centrifugation steps. Rather, the methods of the present disclosure provide for a single step, single density gradient continuous flow centrifugation process to purify AAV and/or rAAV.

In preparation for the experiments disclosed herein, Sf9 cell culture that is commercially available from Expression System, LLC were cultured in shake flasks at 28° C. in ESF921 medium also commercially available from Expression Systems supplemented with 100 units per milliliter penicillin and 100 micrograms per milliliter (µg/ml) streptomycin, commercially available from Mediatech, Inc. The Sf9 cells were split 1:5 once the cell density reached $1 \times 10^7$ cells/ml for maintenance.

The Sf9 cells were cultured to about 8×10⁶ cells/ml and diluted 1:1 with fresh ESF921 media for vector production. Recombinant baculoviruses Bac-inCap2-inRepOpt and Bac-CMV-GFP were used to infect the diluted cells for 3 days and cell pellets were harvested. The cell pellets were stored at −80° C. if not used immediately. The cell pellets were lysed in SF9 lysis buffer (50 mM Tris-HCl, pH7.8, 50 mM NaCl, 2 mM $MgCl_2$, 1% w/v sodium lauroyl sarcosinate, also known as sarkosyl, 0.5% w/v Triton® X-100, and 140 units/ml Benzonase®). Genomic DNA was digested by incubation at 37° C. for one hour. Cell debris was removed by centrifugation at 8,000 rpm (i.e., 10,322×g) for 30 min. The clarified cell lysate (i.e., material) was collected and used for continuous flow centrifugation. Fractions were collected and the quantities of AAV2 vectors (referred to herein as "rAAV") were determined by quantitative PCR (QPCR) method expressed as quantities of viral genomes (vg).

For testing the purification results, SDS-PAGE, silver-staining, and SimplyBlue™ stain were used verify the purity of rAAV. Here, the rAAV were mixed with SDS-PAGE loading buffer, commercially available from Invitrogen, and heated at 95° C. for 5 min. The vectors were then loaded onto a 10% SDS-PAGE Tris-Glycine gel (Invitrogen) and run at 100V until the dye reached the bottom of the gel. The gel was stained according to the manufacturer's protocol (Invitrogen).

Experiment A

It is known from the literature that tube rotor centrifugation of AAV and/or rAAV in a CsCl gradient yields acceptable purity for many applications. It is also known that many gradient materials that are suitable for batch or tube rotor centrifugation are unsuitable for continuous flow centrifugation.

Figure 3:
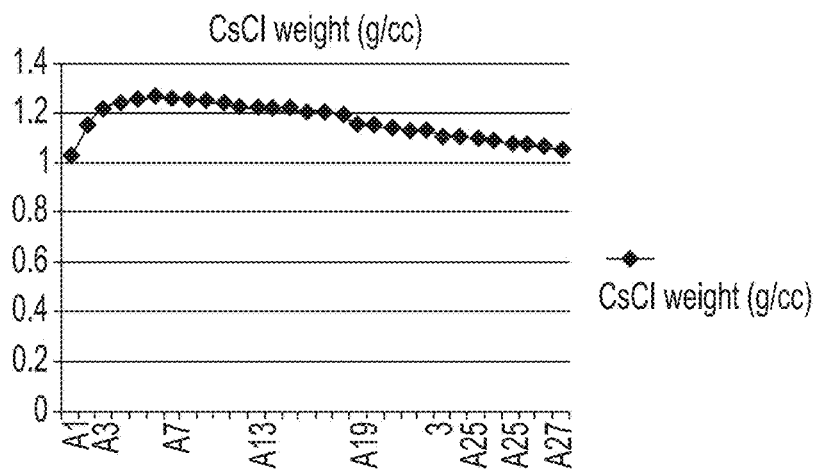
FIG. 3 is a graph illustrating the results of Experiment A.

Referring now to FIG. 3, an initial experiment was designed to test CsCl gradient formation in a continuous flow process—using the AW Promatix 1000™ Here, a CsCl gradient solution was prepared to contain 30% w/v sucrose to increase gradient stability by increasing viscosity. The 120 ml rotor was used and speed was set at 26,000 rpm (i.e., 49,950×g). Next, 30 ml of low density CsCl (1.3 g/cc.) was loaded followed by 38 ml of high density CsCl (1.5 g/cc)—namely Step 1 of FIG. 1. The buffer loading and flush rate was set to 5 ml/min—namely Steps 3 and 4 of FIG. 1—with no AAV or rAAV being loaded. After a 10 min run at operational speeds (Step 4 of FIG. 1), the centrifuge was decelerated and, once the system was at rest, 4 ml volume fractions were collected.

The resultant density of CsCl fractions are shown in FIG. 3. Without wishing to be bound by any particular theory, it is believed by the present disclosure that AAV or rAAV will isopycnically band at the CsCl density of 1.38-1.41 g/cc such that the fractions collected here were lower than the density required for AAV or rAAV to band. Thus, it is believed that the density curve of Experiment A in FIG. 3 lacks the required stability to maintain the required density for the isopycnic banding in continuous flow centrifugation of AAV or rAAV.

Here, it was observed from the CsCl runs that during centrifugation the overall quantity of the CsCl is lost from the stationary gradient phase. This is demonstrated by the fact that the maximum density of CsCl in the rotor is not maintained at the same density as the load concentration. This is considered to be due to 'wash out' of gradient during running, where the interface between the continuous flow phase and the stationary gradient phase is unstable and there is a constant removal of gradient to the flow through and entry of buffer to the stationary phase.

Experiment B

Figure 4:
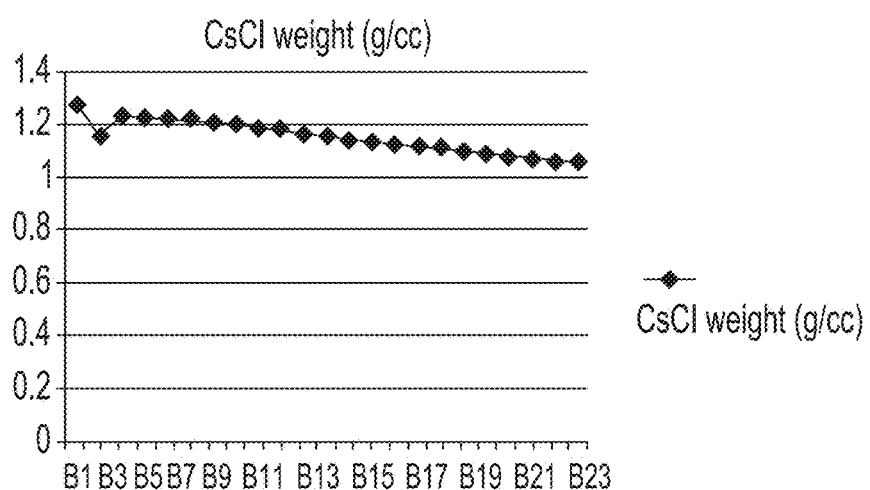
FIG. 4 is a graph illustrating the results of Experiment B.

Referring now to FIG. 4, Experiment A was repeated to confirm CsCl gradient formation for continuous flow centrifugation. Again and as can be seen from the results, even though 1.5 g/cc CsCl was used for the high density gradient, the fractions with the highest density still did not reach the 1.38 g/cc threshold, which means the target vectors would not have formed an isopycnic band if AAV or rAAV had been used in this test.

Experiment C

Figure 5:
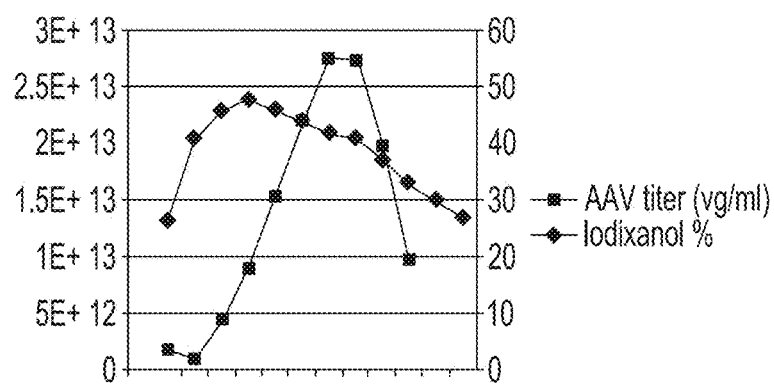
FIG. 5 is a graph illustrating the results of Experiment C.
Figure 6:
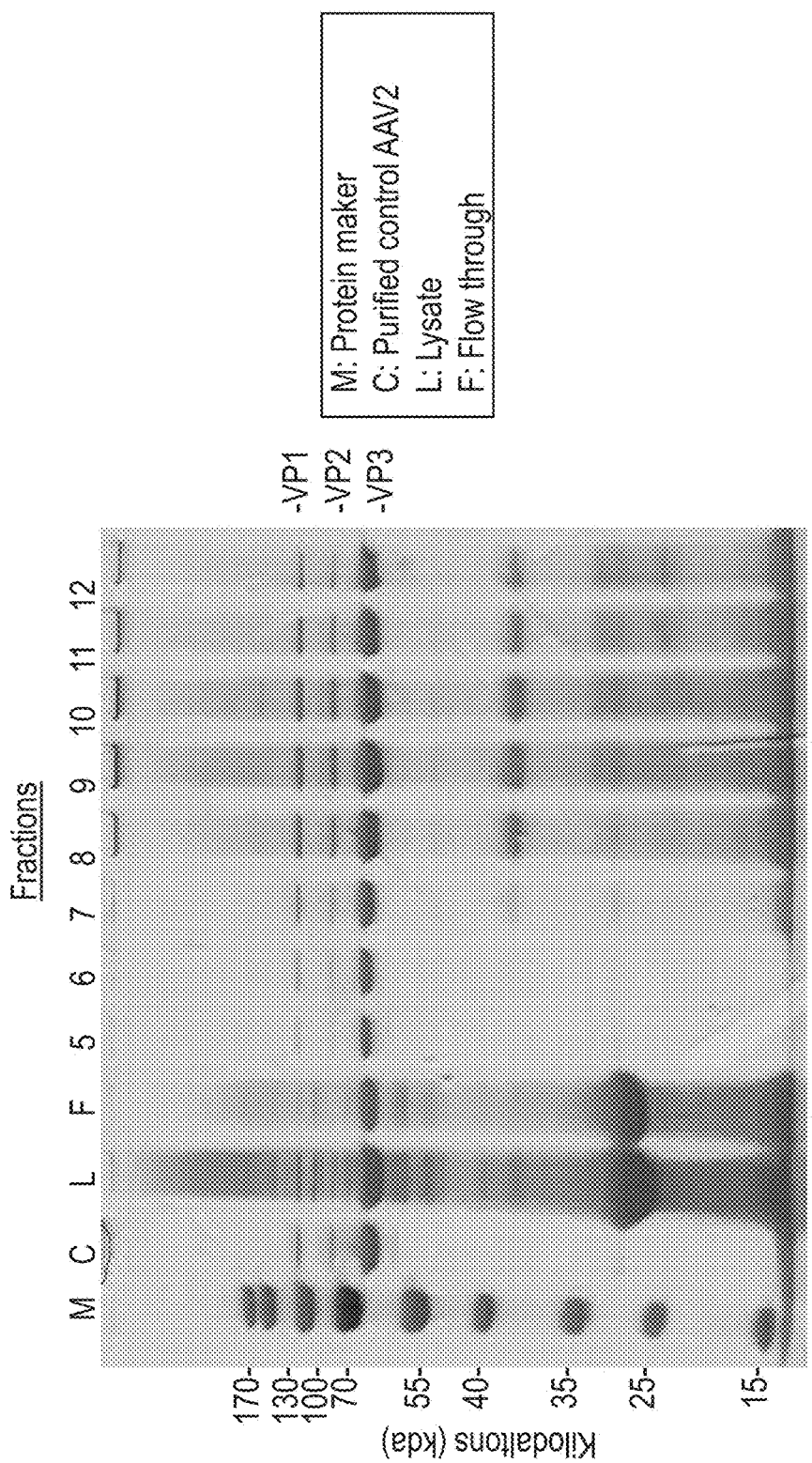
FIG. 6 is an image of sodium dodecyl sulfate polyacrylamide gel electrophoresis (SDS-PAGE) and SimplyBlue™ staining of the Experiment C in FIG. 5.

After the results of Experiment A and Experiment B and still not wishing to be bound by any particular theory, a gradient of iodixanol was attempted for rAAV purification in continuous flow centrifugation as shown in FIGS. 5 and 6.

Here, the 120-ml rotor was used and speed was set at 35,000 rpm (i.e., 90,500×g). The gradient was prepared from 68 ml of 50% w/v iodixanol in distilled water. A total of 100 ml lysate (lot#12-303, total 2.29e+15vg) was used. Material loading rate (Step 3 of FIG. 1) was set at 5 ml/min and the banding or centrifugation time (Step 4 of FIG. 1) was 2 hours. The results of Experiment C are shown in FIG. 5. About 13% of the rAAV loaded was lost to the flow through and the yield in fractions C4 to C11 was 24% of the rAAV loaded. Thus, it can be seen that the majority of the loaded rAAV was lost either in the flow through or by aggregation or by inactivation in the continuous flow centrifugation process.

The data and graph of FIG. 5 illustrate the amount of rAAV that has been collected in vector genomes at each fraction as compared to the total amount of rAAV loaded as vector genomes (vg).

The SDS-PAGE analysis of FIG. 6 compares the results from Lane M, Lane C, Lane L, Lane F, and Lanes 5 through 12.

Lane M illustrates the molecular weight markers for size reference. Lane L represents the lysate used during the experiment, which provides a baseline for the purification. Lane F illustrates the flow through materials that has passed once through the centrifuge rotor during the continuous flow loading of buffer phase.

Lane C illustrates a control purification of the lysate (the "Control"). The fraction of the control lane, Lane C, is used herein as the baseline against which purity is compared. The Control is obtained by a known method of AAV or rAAV purification using a tube rotor and a CsCl gradient.

Lanes C5-C12 represent the collected fractions numbered in FIG. 5, where the bands represented by VP1, VP2, and VP3 indicate the bands of the target vector (i.e., AAV and/or rAAV).

The terms "purity" and "yield" as used herein are discussed with reference to the results of Experiment C shown in FIGS. 5 and 6 for reasons of clarity.

It can be seen from FIG. 6 that the fractions in Lanes C5 and C6 are predominantly represented by the collected target vector as shown by vector proteins VP1, VP2, VP3 with or without the inclusion of the contaminants. The fractions in Lanes C5 and C6 include the target vector in substantially pure form. Thus, the SDS-PAGE of FIG. 6 provides a qualitative measurement of purity confirming the separation of the target vector (VP1, VP2, VP3) from the lysate.

In contrast, the fractions in Lanes C7 through C12, while illustrating better recovery or yield of the target vector than Lanes C5 and C6, these lanes also include one or more contaminants. Thus, the SDS-PAGE analysis of FIG. 6 indicates that the majority of the contaminants were removed from the rAAV, in at least Lanes C5 and C6, after a single continuous flow centrifugation using an iodixanol density gradient.

It can be seen that FIG. 6 illustrates that some material at and below 15 kDa have been collected. Without wishing to be bound by any particular theory, it is believed that the collected materials below 15 kDa represent non-specific fragments and/or degradation products (referred to herein as "debris") that may be a function of sample preparation and may not detrimental or otherwise undesired in the downstream uses/processing of the target vector. In some embodiments, the definition of purity ignores the presence of the debris.

The term "yield" shall mean the percentage of the collected target vector (i.e., AAV and/or rAAV) as a function of the total vector loaded in vector genomes for all lanes. In some embodiments, only those lanes that meet a desired purity are considered as the "purified yield". Graphically, the "yield" is shown in FIG. 5 as the entire area under the rAAV titer curve—which represents about 24% of the total vector loaded, whereas the results for Lanes C5 and C6 can be considered to provide a "pure yield"—which represents about 4% of the total vector loaded. The yield as used herein is also expressed, in some instances, as the recovery of the process.

FIG. 6 can also be used to better understand the term "predictable contaminant" as defined above. Looking to Lanes C8 through C10, it can be seen that as the quantity of target vector, as represented by vector proteins (VP1, VP2, VP3), increases, so does the amount of a specific contaminant at about 40 kDa. Looking to Lanes C11 and C12, it can be seen that as the quantity of target vector, as represented by vectors proteins (VP1, VP2, VP3), decreases, so does the amount of the specific contaminant at about 40 kDa. Thus, in Experiment C it can be observed that the specific contaminant at about 40 kDa is predictable or co-purifies with the target vector, namely is a predictable contaminant.

Returning for a moment to the term "purity" or "pure" as used herein, it is contemplated by the present disclosure that—in some embodiments—the predictable contaminant may be acceptable for the particular downstream purification of the target vector. In these embodiments, the definition of purity includes the collected predictable contaminant in the calculation of the percentage of separated viral vectors (i.e., the yield includes the separated viral vector and the predictable contaminant, but does not include any other contaminants).

Experiment D

Based on the result of Experiment C discussed above, two density gradient layers of iodixanol were used to see if more contaminants could be removed—with all materials being prepared in distilled water. The low density layer of 25 ml of 25% w/v iodixanol and the high density layer of 58 ml of 50% w/v iodixanol were loaded. The 120-ml rotor was used and a new lot of cell lysate (lot#14-130, total 2.09e+14vg) was prepared. The speed was set to 35,000 rpm (i.e., 90,500×g) and banding time (Step 4 of FIG. 1) was 2 hours. The material loading rate was 5 ml/min (Step 3 of FIG. 1) and flush rate of flow through buffer (Step 4 of FIG. 1) was 5 ml/min (Step 7 of FIG. 1).

Figure 7:
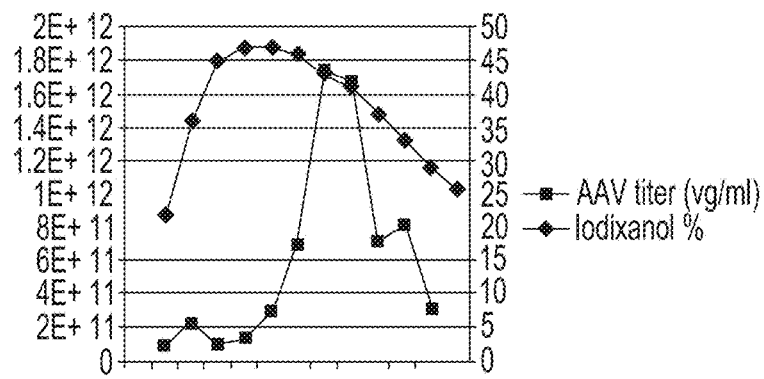
FIG. 7 is a graph illustrating the results of Experiment D.
Figure 8:
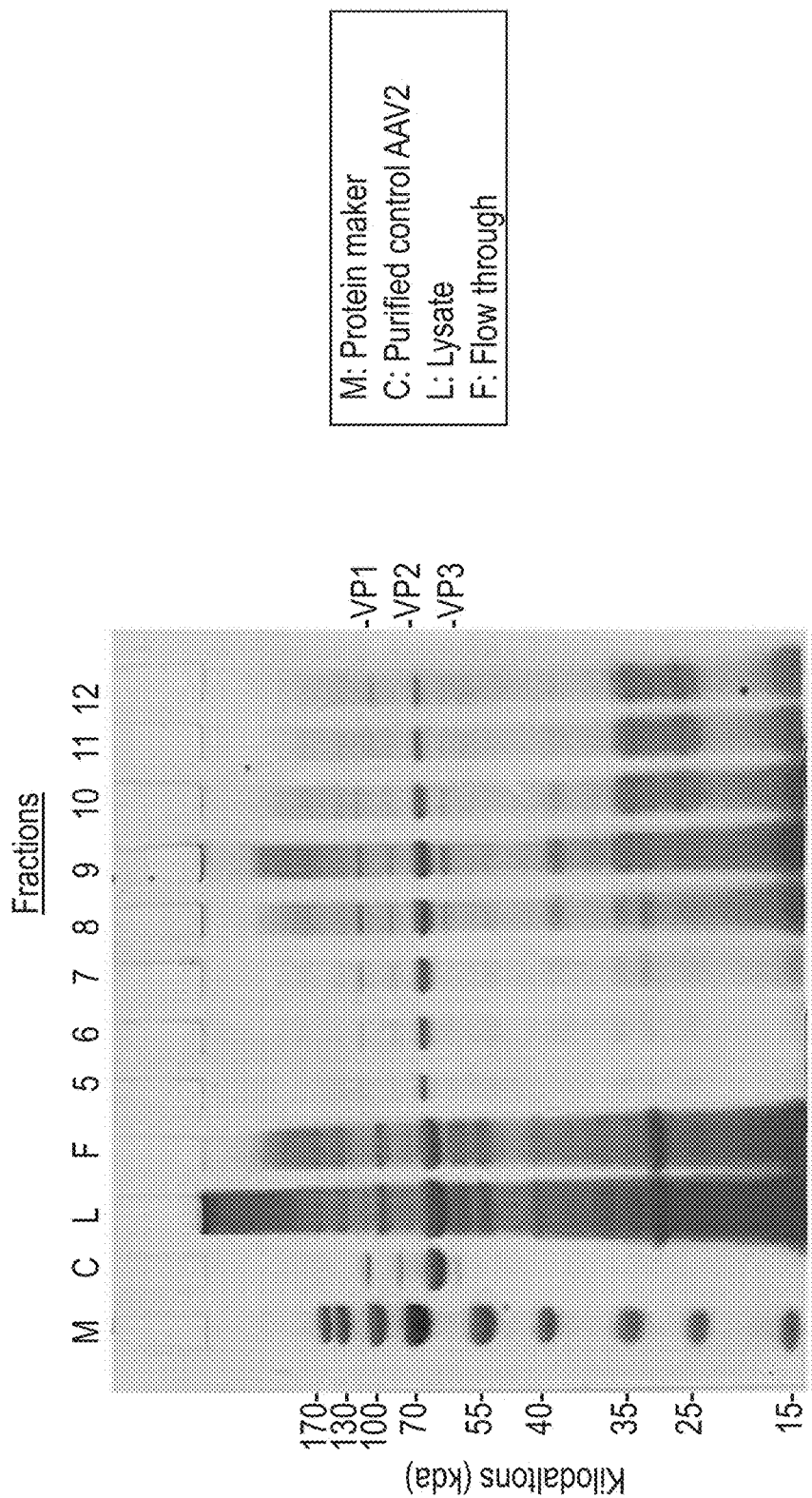
FIG. 8 is an image of SDS-PAGE and SimplyBlue™ staining of the fractions of Experiment D in FIG. 7.

The results are shown in FIGS. 7 and 8. Here, it can be seen that the rAAV concentration in the lysate was 10 times lower than the previous lysate. While there was a sharp rAAV purification curve, the yield or recovery of fractions collected from D6 to D12 was only 12%. However and because of the low rAAV titer used, the SDS-PAGE of FIG. 8 did not show clear vector protein (VP1, VP2, VP3) bands of rAAV.

The SDS-PAGE analysis of FIG. 8 indicates that the majority of the contaminants were removed from the rAAV, in at least Lanes D5-D7, after a single continuous flow centrifugation. Stated another way, the fractions examined in Lanes D5-D7 include the target vector in pure form. Here, about 15% of the rAAV loaded was lost to the flow through and the recovery or yield in fractions D2 to D12 was 12% of the rAAV loaded.

Experiment E

Next, the test using a two-layer gradient as in Experiment D was repeated using a 230-ml rotor to determine whether the results of Experiment D can be scaled linearly for rAAV purification. Here, the two layer iodixanol solution was prepared with phosphate-buffered saline (PBS) buffer. The 40 ml of 25% w/v and 98 ml of 50% w/v iodixanol were loaded in the 230-ml rotor (Step 1 of FIG. 1). The speed was set to 35,000 rpm (i.e., 90,500×g) and banding time was for 2 hours (Step 4 of FIG. 1). The material loading speed was set to 10 ml/min (Step 3 of FIG. 1) and flow through buffer flush rate was set to 5 ml/min (Step 7 of FIG. 1). A total of 160 ml of lysate (lot#14-130) was loaded.

Figure 9:
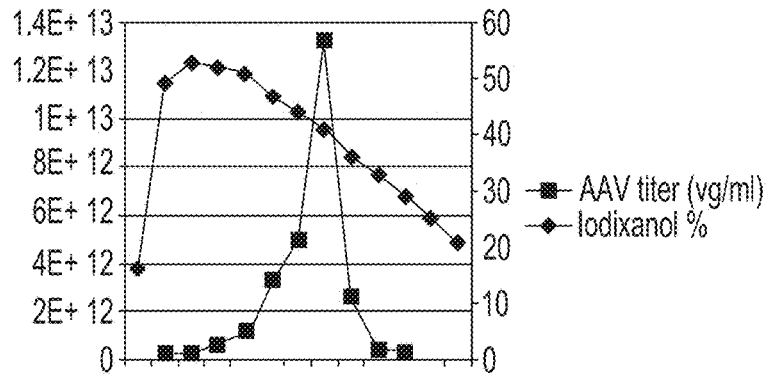
FIG. 9 is graph illustrating the results of Experiment E.
Figure 10:
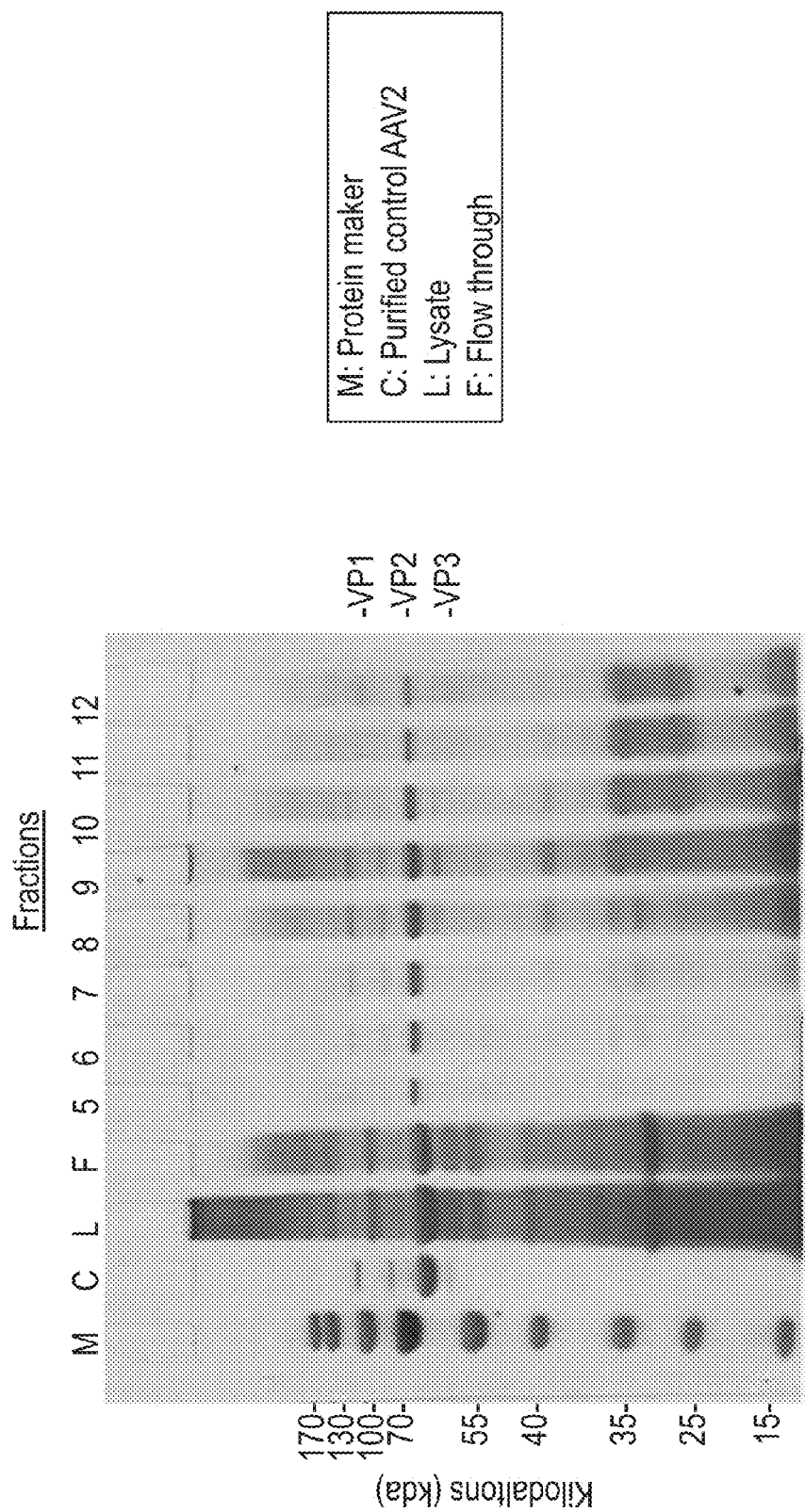
FIG. 10 is an image of SDS-PAGE and SimplyBlue™ staining of the fractions of Experiment E in FIG. 9.

The results are shown in FIGS. 9 and 10. It can be seen from the results that a sharp rAAV purification curve was obtained. The recovery rate of fractions collected from E5 to E9 was 65% w/v when iodixanol was prepared in PBS. The SDS-PAGE of FIG. 10 showed the rAAV clearly, indicating a better recovery or yield as compared with Experiment D.

The SDS-PAGE analysis of FIG. 10 indicates that the majority of the contaminants were removed from the rAAV, in at least Lanes E5-E7, after a single continuous flow centrifugation. Stated another way, the fractions in Lanes E5-E7 include the target vector in pure form. Here, about 22% of the rAAV loaded was lost to the flow through and the yield in fractions E2 to E11 was 65% of the rAAV loaded.

It can be seen from Experiment E that preparation of the iodixanol gradient with PBS buffer—instead of distilled water as in Experiments C and D—provided a higher yield. However, Experiment E also reveals that the predictable contaminant, which was present at about 40 kDa in both Experiments C and D, is still present. Since the gradients formed in the 120 ml and 230 ml rotors were substantially the same with the viral vector banded at the same position and the slope of the gradient being similar when compared, the purification process disclosed herein is scalable among cores of different volumes.

Experiment G

In Experiment G, Fractions C3 through C12 from Experiment C were pooled to provide a total of 42.5 ml. The refractive index of the pooled solution was 1.3951, which corresponds to about 33% w/v of iodixanol. The material was diluted 3 times to decrease the iodixanol concentration to about 10% w/v and a second centrifugation was performed to see if the purity of the rAAV could be improved. The 120-ml rotor was used and speed was set to 35,000 rpm (i.e., 90,500×g). 25 ml of 25% w/v and 58 ml of 50% w/v iodixanol were loaded (Step 1 of FIG. 1). A total of 127.5 ml diluted material was loaded (Step 3 of FIG. 1). Material loading rate (Step 3 of FIG. 1) and buffer flush rate (Step 7 of FIG. 1) were set to 5 ml/min. Banding time (Step 4 of FIG. 1) was set to 2 hours.

Figure 11:
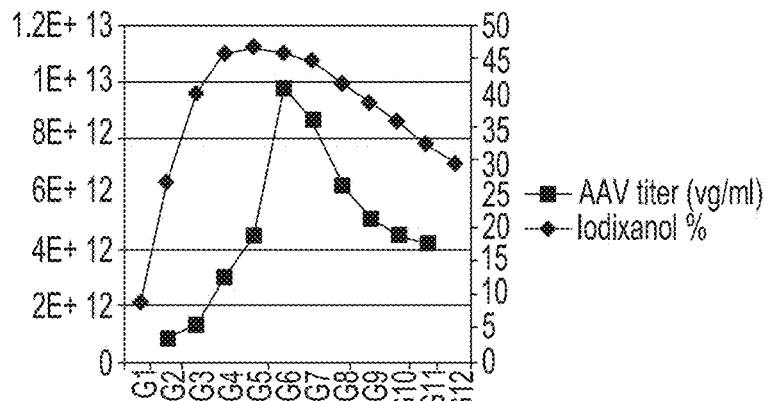
FIG. 11 is a graph illustrating the results of Experiment G.
Figure 12:
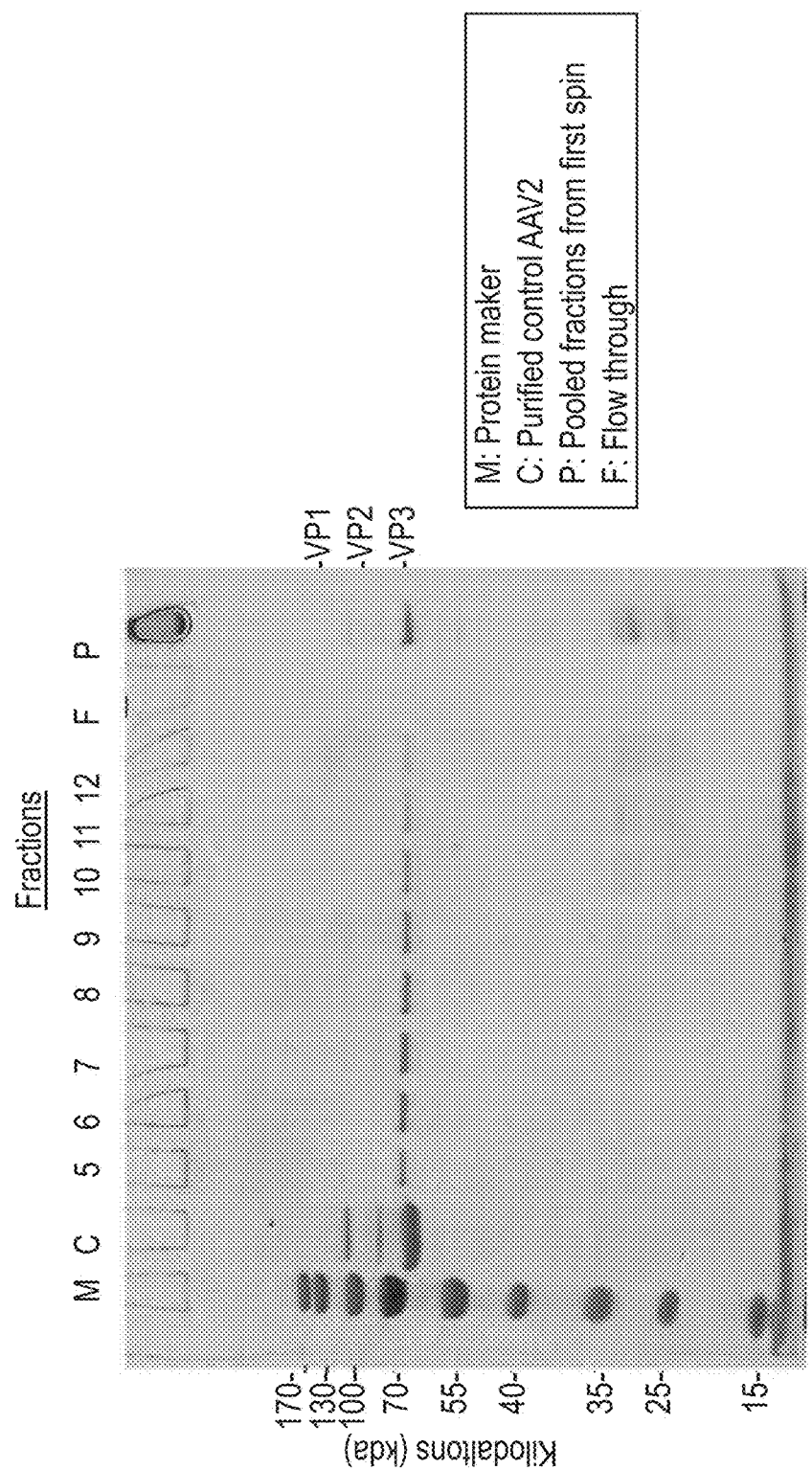
FIG. 12 is an image of SDS-PAGE and SimplyBlue™ staining of the fractions of Experiment G in FIG. 11.

The results of Experiment G are shown in FIGS. 11 and 12, which indicate that the second continuous flow centrifugation yielded purer rAAV.

The SDS-PAGE analysis of FIG. 12 indicates that the majority of the contaminants were removed from the rAAV, in Lanes G5 through G12, after the second continuous flow centrifugation. Stated another way, the fractions in Lanes G5 through G12 include the target vector in pure form. Here, about 45% of the rAAV loaded was lost to the flow through and the recovery in fractions in Lanes G5 through G12 was 49% of the rAAV loaded (i.e., 49% yield of pure or separated viral vector).

FIG. 12 further indicates the presence of debris at and below 15 kDa, but appears to lack the predictable contaminant noted in Experiment C.

Experiment H

In Experiment H, another lot of rAAV lysate, namely lot#14-172, was produced and a centrifugation run was performed using the 120-ml rotor. The speed was set to 35,000 rpm (i.e., 90,500×g) and banding time (Step 4 of FIG. 1) was 2 hours. The gradient included 25 ml of 25% w/v iodixanol and 58 ml of 50% w/v iodixanol. A total of 95 ml lysate (total rAAV 1.25e+15vg) was used. Material loading (Step 3 of FIG. 1) and flow through buffer flush rate (Step 7 of FIG. 1) were set to 5 ml/min. PBS buffer and iodixanol were prepared to contain 100 mM sodium citrate. Without wishing to be bound by any particular theory, the variances in yield observed in Experiments C through G may be due to aggregation of the target vector. Thus, Experiment H has included sodium citrate in an attempt to minimize aggregation.

Figure 13:
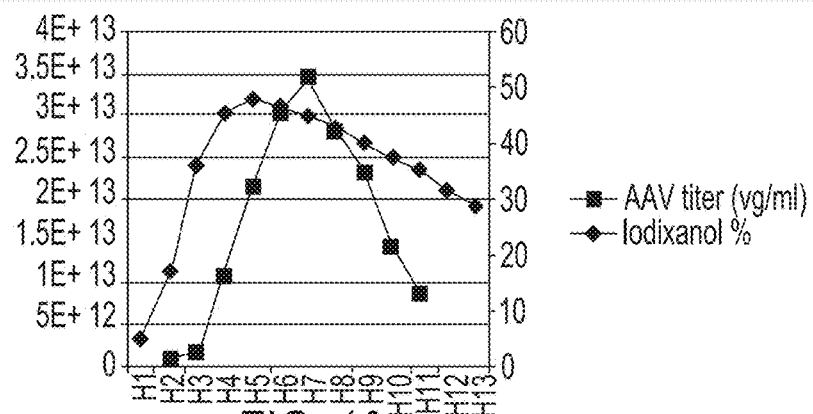
FIG. 13 is a graph illustrating the results of Experiment H.
Figure 14:
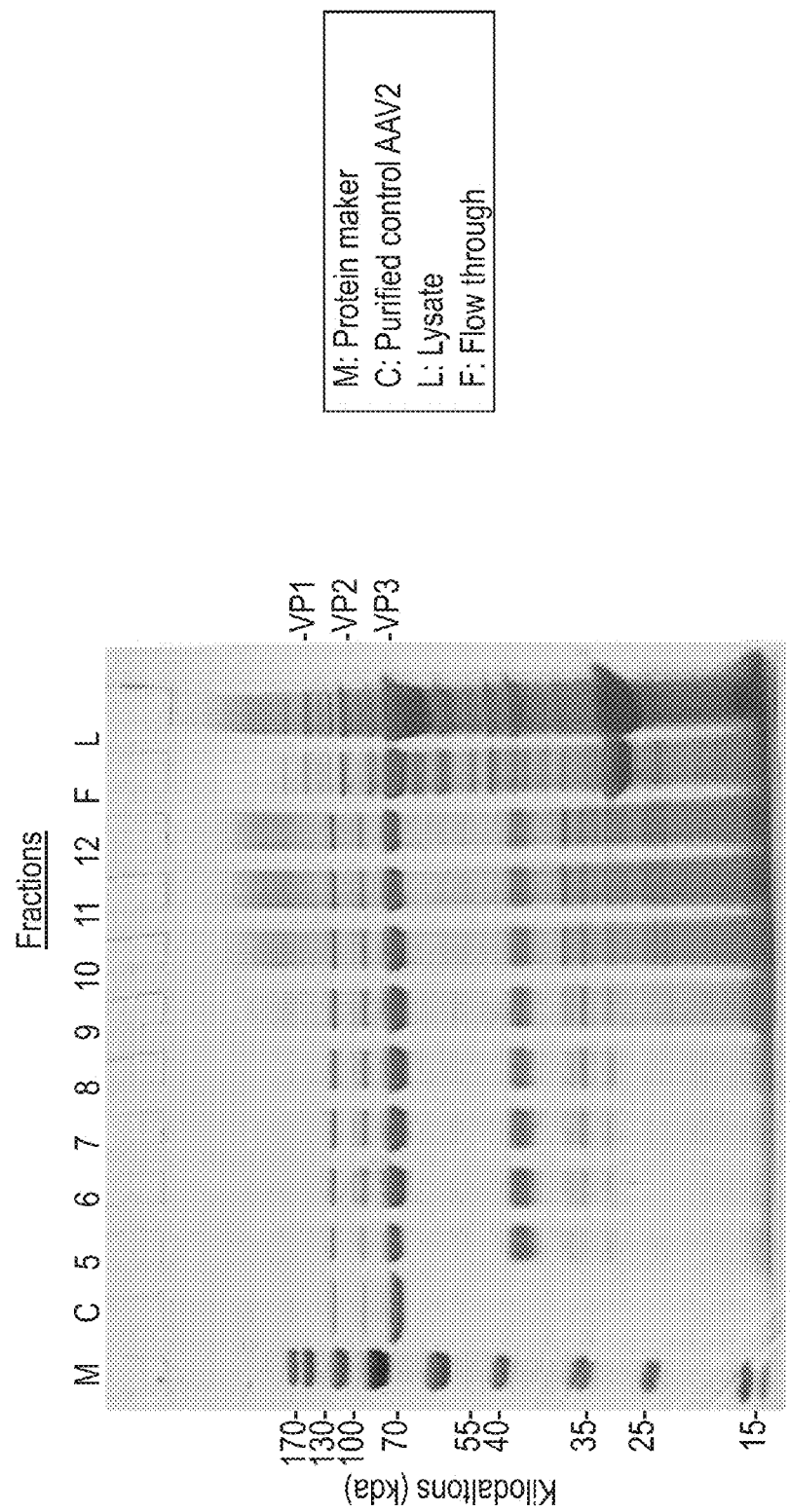
FIG. 14 is an image of SDS-PAGE and SimplyBlue™ staining of the fractions of Experiment H in FIG. 14.

The results of Experiment H are shown in FIGS. 13 and 14. The SDS-PAGE analysis of FIG. 14 indicates that the majority of the contaminants were removed from the rAAV, in Lanes H5 through H8, after the single continuous flow centrifugation. Stated another way, the fractions in Lanes H5 through H8 include the target vector in substantially pure form.

It is noted that Lanes H5 through H8 include both debris below 15 kDa and the predictable contaminant at about 40 kDa—which, for the purposes of determining yield of Experiment H, have been discounted. Here, about 32% of the rAAV loaded was lost to the flow through and the recovery in fractions H2 through H11 was 55% of the rAAV loaded.

It is also noted that the sodium citrate of Experiment H, as shown from the results of FIGS. 13 and 14, is believed to reduce aggregation of the target vector.

Experiment I

The fractions from Experiment E, namely lot #14-130, was pooled together with another similar run to obtain 67 ml of rAAV solution and diluted 10 fold to decrease the iodixanol concentration to about 3% (w/v). Experiment I was conducted to test if lowering the concentration of iodixanol in the material would, enable the rAAV to more easily enter the density gradient phase and to minimize the rAAV from being lost to the flow through buffer exiting the rotor. The 120-ml rotor was used and the speed was set to 35,000 rpm (i.e., 90,500×g) and 25 ml of 25% w/v and 58 ml of 50% w/v iodixanol were added. The material loading flow rate was set to 10 ml/min and flow through buffer flush rate was 5 ml/min. The banding time was 2 hours.

Figure 15:
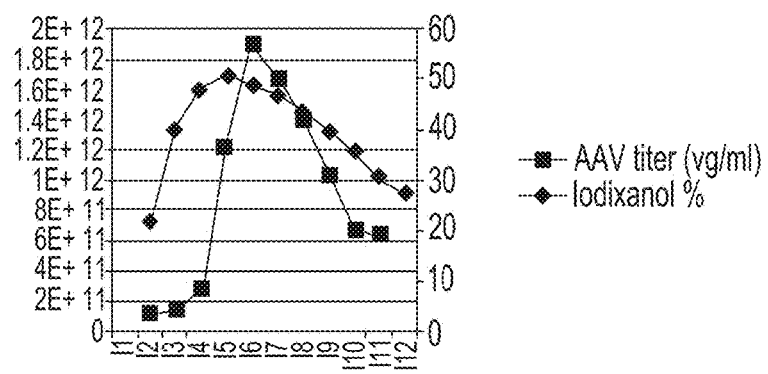
FIG. 15 is a graph illustrating the results of Experiment I.
Figure 16:
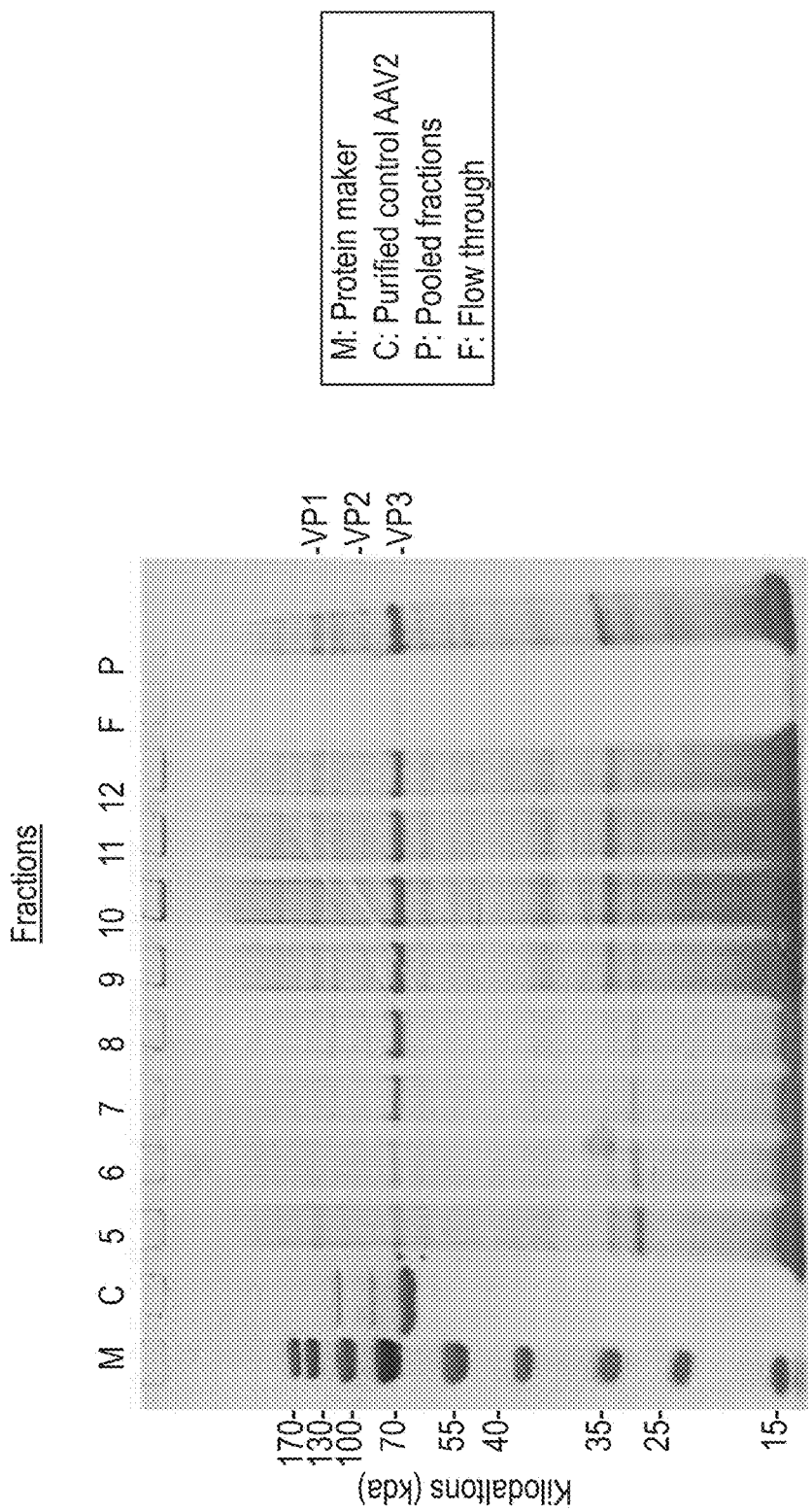
FIG. 16 is an image of SDS-PAGE and SimplyBlue™ staining of the fractions of Experiment I in FIG. 15.

The results of Experiment I are shown in FIGS. 15 and 16. The SDS-PAGE analysis of FIG. 16 indicates that the majority of the contaminants were removed from the rAAV, in Lanes I7 and I8, after the second continuous flow centrifugation. Stated another way, the fractions in Lanes I7 and I8 include the target vector in pure form.

It is noted that Lanes I5 through I12 include both debris below 15 kDa and a predictable contaminant at bands between 25 and 35 kDa—which, for the purposes of determining yield of Experiment I, have been discounted. Here, about 7% of the rAAV loaded was lost to the flow through and the recovery in fractions I2 through I11 was 4% of the rAAV loaded. Without wishing to be bound by any particular theory, it is believed that the low recovery of Experiment I was, at least in part, due to the low concentration of the rAAV loaded—due to the pooling of the results of Experiment E and another similar run.

Experiment J

The fractions from Experiment H were pooled to 43 ml and a second centrifugation was performed using the 120-ml rotor. The material was diluted 10 fold to a volume of 430 ml in PBS buffer containing 100 mM sodium citrate. The speed was set to 35,000 rpm (i.e., 90,500×g) and banding time was 2 hours and 68 ml of 50% w/v iodixanol was loaded. Material loading and buffer flush rate was set to 5 ml/min.

Figure 17:
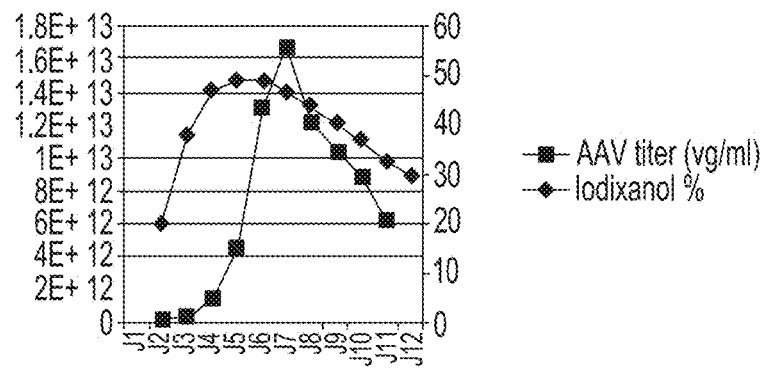
FIG. 17 is a graph illustrating the results of Experiment J.
Figure 18:
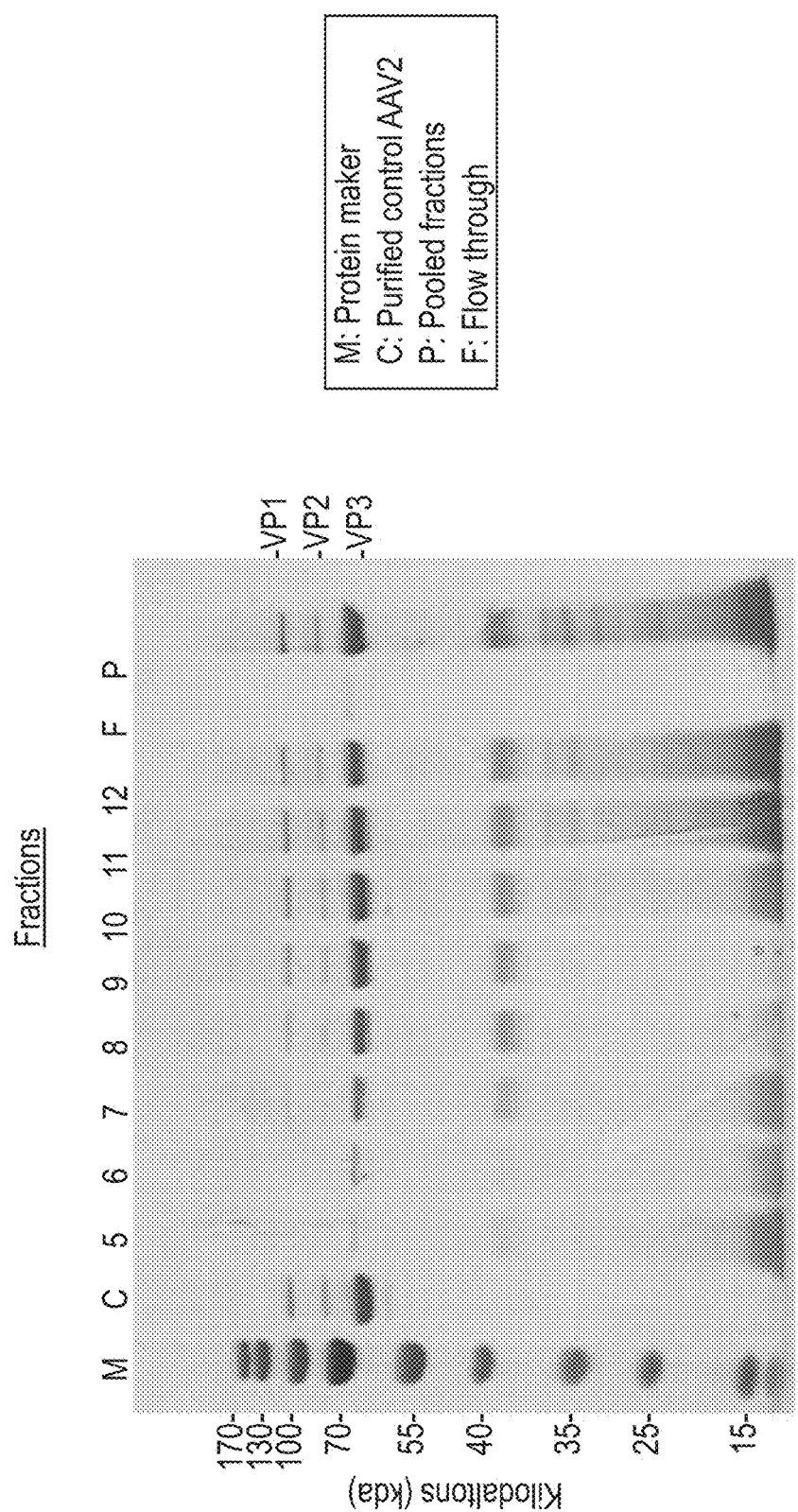
FIG. 18 is an image of SDS-PAGE and SimplyBlue™ staining of the fractions of Experiment J in FIG. 17.

The results of Experiment J are shown in FIGS. 17 and 18. The SDS-PAGE analysis of FIG. 18 indicates that the majority of the contaminants were removed from the rAAV, in Lanes J5 through J9, after the second continuous flow centrifugation. Stated another way, the fractions in Lanes J5 through J9 include the target vector in pure form.

It is noted that Lanes J9 through J12 include both debris below 15 kDa and a predictable contaminant at bands between 40 and 35 kDa—which, for the purposes of determining yield of Experiment J, have been discounted. Here, about 24% of the rAAV loaded was lost to the flow through and the recovery in fractions J2 through J11 was 43% of the rAAV loaded.

It is believed that the results of Experiments G, I, and J illustrate that a second centrifugation step is un-necessary—such that the process of the present application can provide AAV and/or rAAV at a desired purity in a single step.

Experiment K

In Experiment K, the other half lot of rAAV lysate from lot #14-172 was used to repeat the centrifugation run of Experiment H with the 120-ml rotor. The speed of the centrifugation was set to 35,000 rpm (i.e., 90,500×g) and the density gradient was allowed to orient and linearize. The banding time was 2 hours and 25 ml of 25% w/v and 58 ml of 50% w/v iodixanol were loaded. A total of 95 ml lysate (total rAAV 1.25e+15vg) was used. Material loading and buffer flush rate was set to 5 ml/min. PBS buffer and iodixanol were prepared to contain 100 mM sodium citrate to aid in prevention of aggregation of the target vector as proven from Experiment H above.

Figure 19:
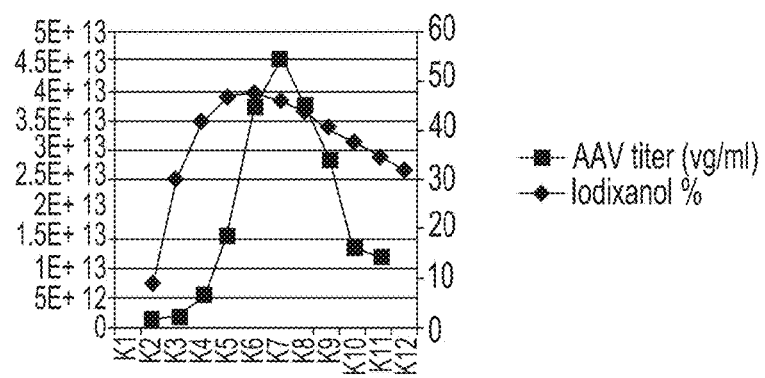
FIG. 19 is a graph illustrating the results of Experiment K, which exposes the other half of the fraction used in Experiment H to a continuous flow centrifugation step.
Figure 20:
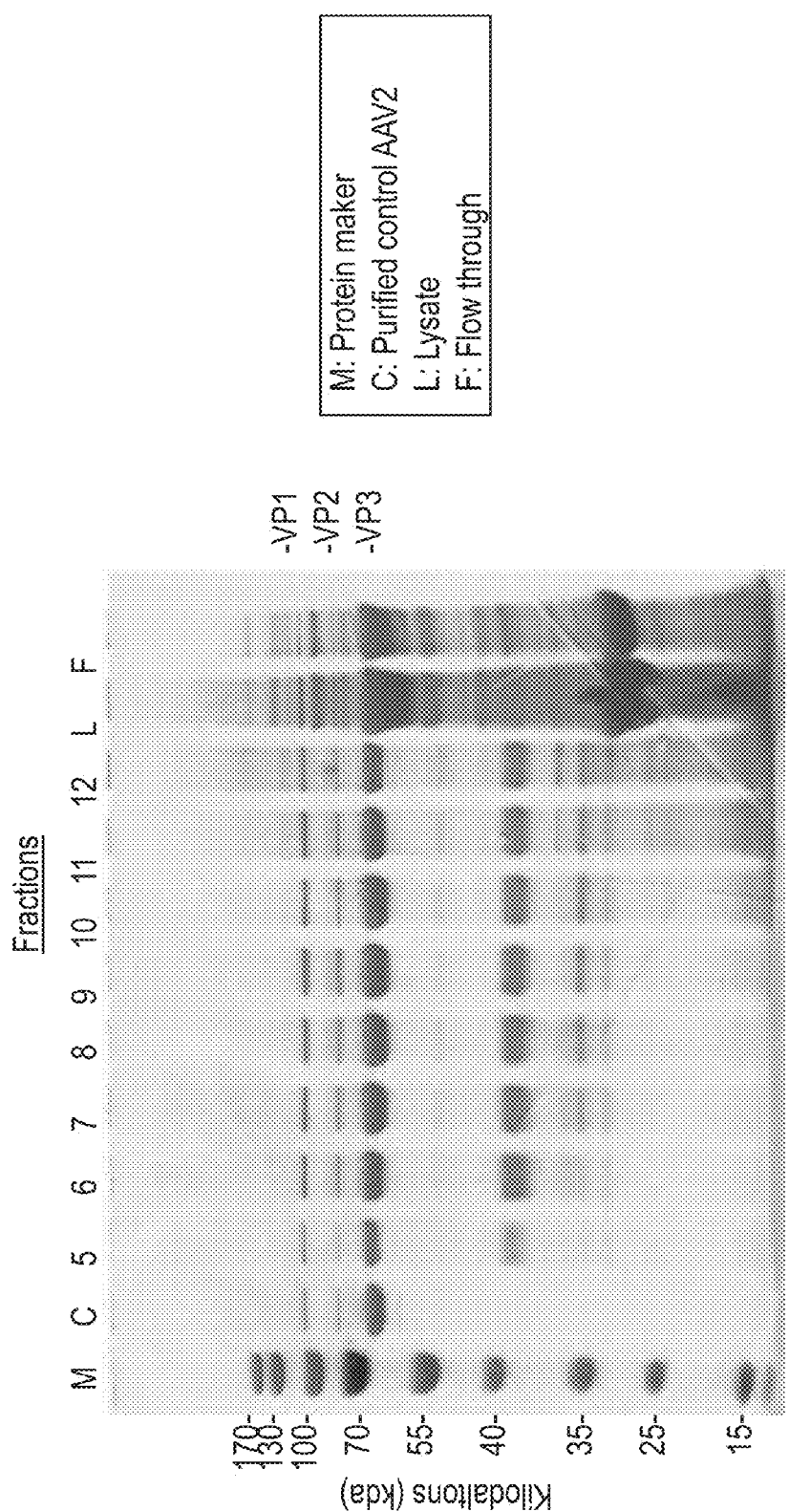
FIG. 20 is an image of SDS-PAGE and SimplyBlue™ staining of the fractions of Experiment K in FIG. 19.

As shown in FIGS. 19 and 20, the results of Experiment K show rAAV purification, but again with predictable contamination bands.

In FIG. 20, the purified rAAV was collected and mixed with SDS-PAGE loading buffer commercially available from Invitrogen and heated at 95 degrees Celsius for 5 minutes and then loaded onto a 10% w/v SDS-PAGE Tris-Glycine gel also commercially available from Invitrogen and were run at 100V until the dye reached the bottom of the gel. The gel was stained according to the manufacturer's protocol (Invitrogen). Here, it can be seen that the results confirm purification of rAAV from the lysate in a single continuous flow centrifugation process.

The SDS-PAGE analysis of FIG. 20 indicates that the majority of the contaminants were removed from the rAAV, in Lanes K5 through K9, after the continuous flow centrifugation. Stated another way, the fractions in Lanes K5 through K9 include the target vector in pure form.

It is noted that Lanes K5 through K12 includes predictable contaminant between 40 and 35 kDa—which, for the purposes of determining yield of Experiment K, have been discounted. Here, about 29% of the rAAV loaded was lost to the flow through and the recovery in fractions K2 through K11 was 47% of the rAAV loaded.

Accordingly, Experiments A through K above illustrate the success of a one-step scalable procedure for purification of adeno-associated virus (AAV) using a continuous flow centrifuge and an unmodified iodixanol density gradient. The results using the unmodified iodixanol density gradient also illustrated purifications that contained predictable contaminant.

In some embodiments and depending on the end use of the purification of the AAV and/or rAAV, the recovery and purification with the presence of the predictable contaminant of Experiments A through K may be within acceptable parameters for some processes. Here, the present application provides for such results in a single continuous flow centrifugation in an unmodified iodixanol gradient, preferably in a PBS buffer with sodium citrate.

In other embodiments and depending on the end use of the purification of the AAV and/or rAAV, the predictable contaminant may not be within acceptable parameters. Methods other than the one and two continuous flow centrifugations discussed above were tested to determine various parameters for removing the remaining contaminants.

Figure 21:
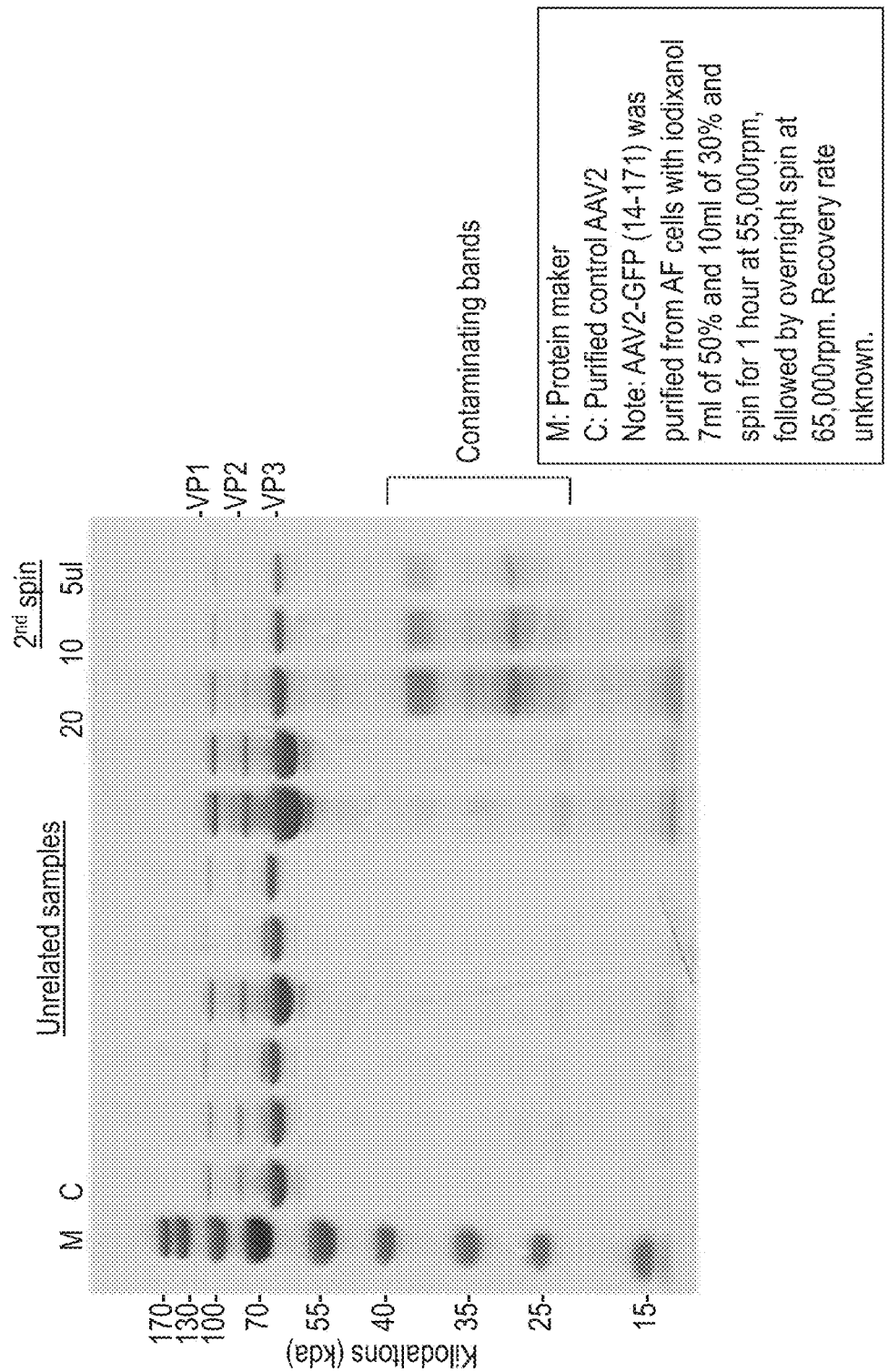
FIG. 21 is an image of SDS-PAGE and SimplyBlue™ staining of the fractions after a tube rotor centrifugation in an iodixanol gradient.

The results shown in FIG. 21 were obtained by exposing lysate to an overnight tube rotor centrifugation using an iodixanol gradient having 7 ml of 50% w/v and 10 ml of 30% w/v iodixanol with a 1-hour centrifugation at 55,000 rpm (i.e., 340,000×g) followed by an overnight centrifugation at 65,000 rpm (i.e., 402,000×g). Here, it can be seen that the contaminating bands remain even after the second tube rotor centrifugation step.

Without wishing to be bound by any particular theory, it is theorized by the present application that the contamination bands, which remains regardless of whether purified via a single continuous flow centrifugation (Experiment K—FIG. 20) alone or followed by a long duration rotor centrifugation (FIG. 21) or is purified by two separate continuous flow centrifugations (Experiments G, I, and J), is not due to the continuous flow centrifuge but could be due, at least in part, to the nature of the gradient agent, iodixanol.

Figure 22:
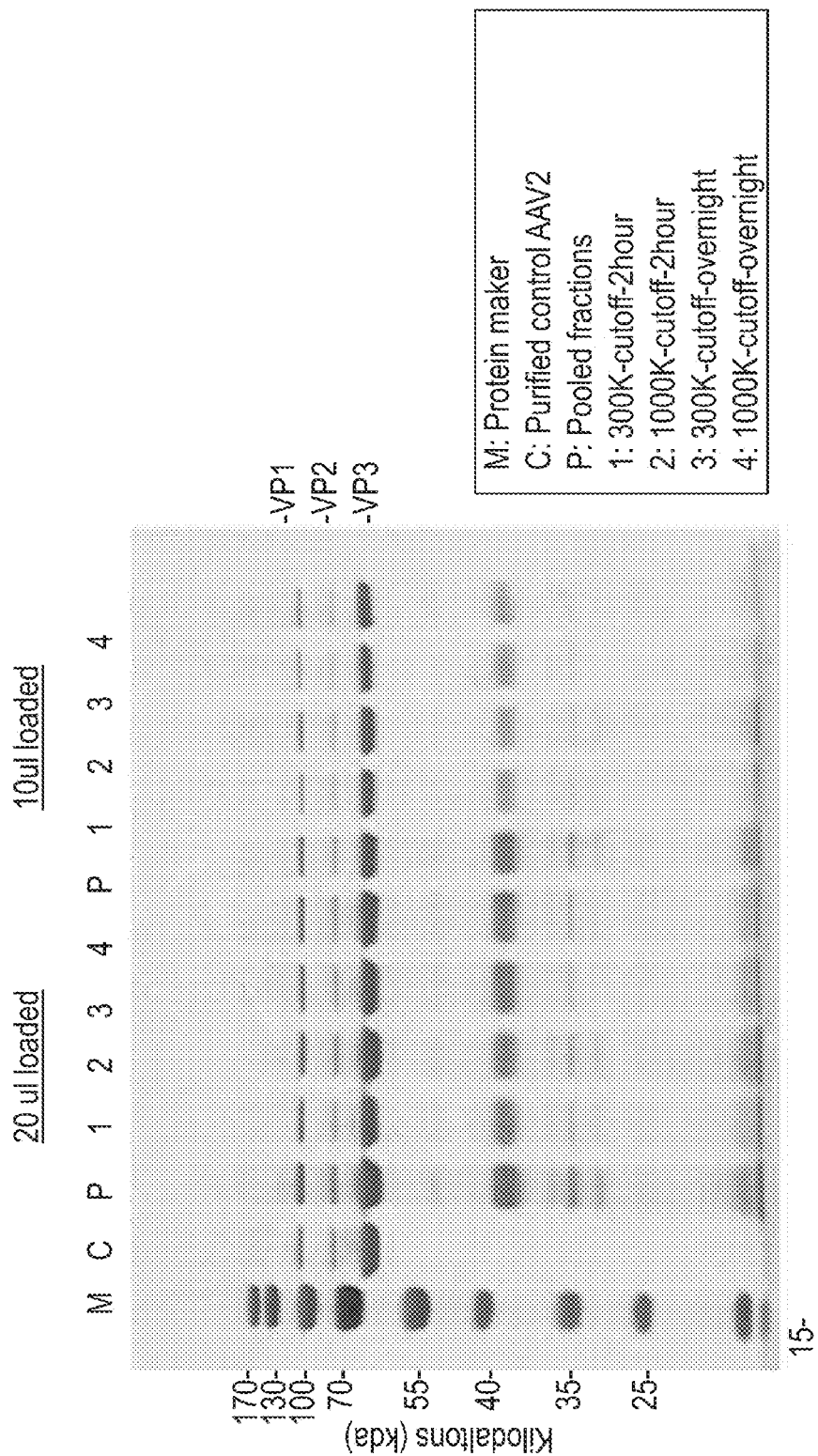
FIG. 22 is an image of SDS-PAGE and SimplyBlue™ staining of the fractions obtained from Experiment H after a dialysis purification step.

The results in FIG. 22 were obtained by pooling the fractions from Experiment H discussed above and exposing the resultant pooled lysate to a dialysis purification, which is an often used and well known method for removing smaller contaminants such as the predictable contaminant discussed above.

The dialysis used the Float-a-Lyzer cassette with a molecular weight cutoff at 1,000 kDa or 300 kDa—with the hypothesis that the desired rAAV with an estimated molecular weight of 3,900 kDa would remain inside the cassette and the smaller contaminants would diffuse into the dialysis buffer and be removed. The dialysis used 1 ml material in 100 ml PBS buffer for 2 hours, another 1000 ml PBS was replaced and dialysis overnight. The rAAV inside the cassette were recovered and titrated with qPCR.

The SDS-PAGE was then performed to determine the purity of the collected target vector with the results of FIG. 22 illustrating the dialysis was not effective at removing the contaminants.

In view of the above and without wishing to be bound by any particular theory, it was hypothesized that the predictable contaminant could be proteins that are bound to and, thus, co-purifying with, the rAAV such that strong ionic conditions such as, but not limited to, caesium chloride or high concentration of salt, could be effective at dissociating the predicable contaminants from the target vector—either before, during, or after the one-step continuous flow centrifugation process.

Figure 23:
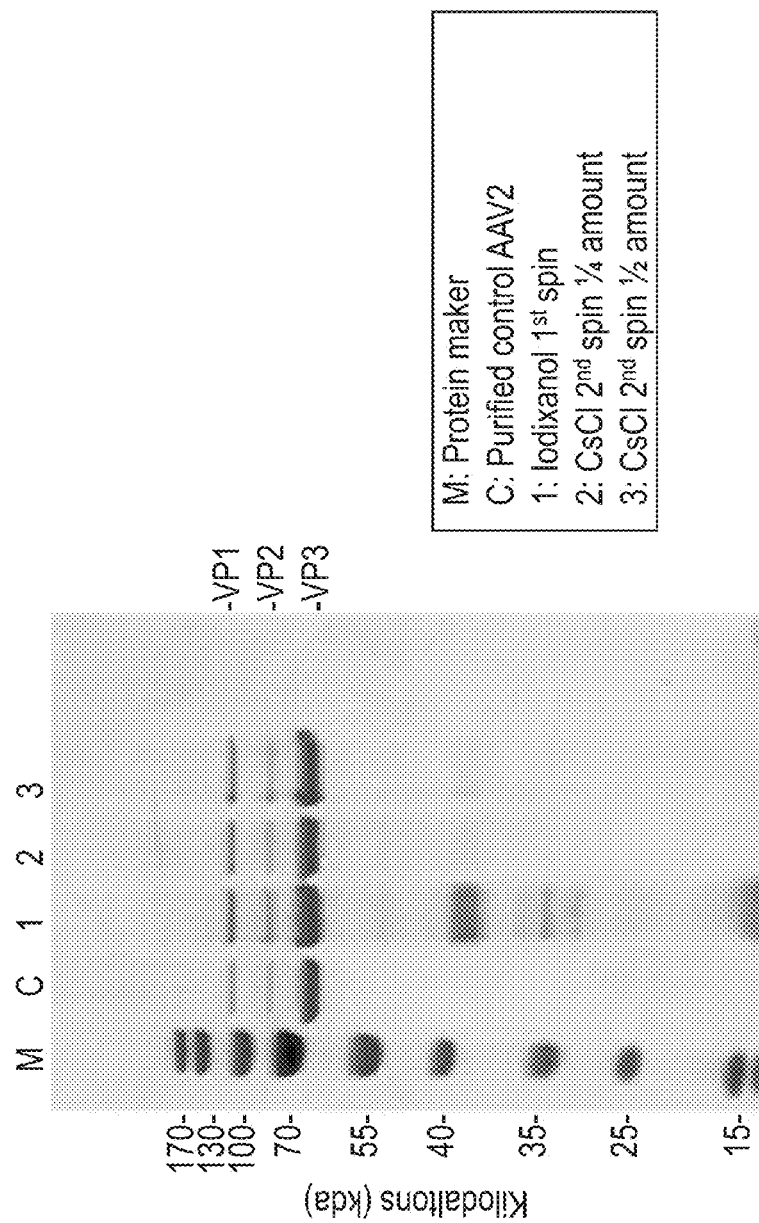
FIG. 23 is an image of SDS-PAGE and SimplyBlue™ staining of the fractions after an additional tube rotor centrifugation with a caesium chloride modifier.

The results in FIG. 23 were obtained by repeating Experiment H discussed above and exposing the resultant fraction pool to a dialysis purification, to remove the iodixanol, as discussed above with respect to FIG. 22, followed by tube rotor centrifugation at 65,000 rpm (i.e., 402,000×g) overnight in a gradient including caesium chloride (CsCl). As shown by FIG. 23, the predictable contaminating band was no longer present.

Figure 24:
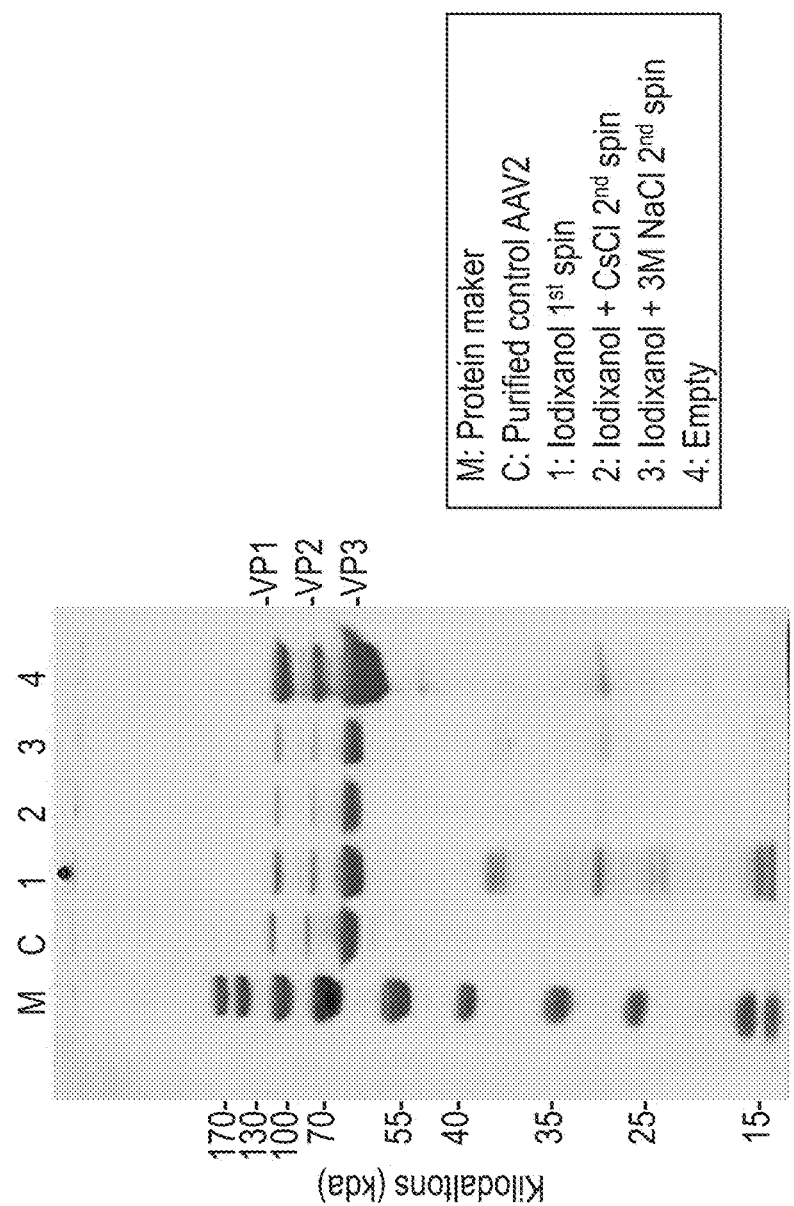
FIG. 24 is an image of SDS-PAGE and SimplyBlue™ staining of the fractions after a tube rotor centrifugation with a caesium chloride modifier.

The results in FIG. 24 were obtained by repeating Experiment H discussed above but eliminating the dialysis, as discussed above with respect to FIGS. 22 and 23, but rather following the continuous flow centrifugation of Experiment H with the tube rotor centrifugation at 65,000 rpm (i.e., 402,000×g) overnight in a gradient including caesium chloride (CsCl)—shown in lane 2. As shown by FIG. 24, the contaminating band was eliminated by the centrifugation in the presence of CsCl.

As an additional test also shown by FIG. 24, the continuous flow centrifugation of Experiment H was also followed by tube rotor centrifugation at 65,000 rpm (i.e., 402,000×g) overnight in a gradient including 3M sodium chloride (NaCl) shown in lane 3. The contaminating band was eliminated by the centrifugation in the presence of NaCl.

As shown from the results in FIGS. 23 and 24, when it is desired to remove the predictable contaminant present after a single continuous flow centrifugation in iodixanol, the present application was successful by using ionic conditions—via a second rotor centrifugation in CsCl and NaCl—to disassociate or otherwise remove the predictable contaminant.

While it has been illustrated in the results of FIGS. 23 and 24 that it is possible to remove or disassociate or otherwise remove the predictable contaminant by exposure to ionic conditions in a purification step that occurs after exposure to the continuous flow centrifugation step, it is also contemplated by the present disclosure for such ionic conditions to be present before or during the exposure to the continuous flow centrifugation step.

Experiment L

A lysate was prepared from 1000 ml cell culture of Lot#15-219, with an estimated 2e+15vg rAAV. This lysate was stored at 4 degrees C. for about 2 weeks prior to usage. Immediately before use, NaCl was added to the lysate to a final 3M concentration and then the material was processed in the continuous flow centrifugation purification. The volume of the lysate was 100 ml. A 120 ml rotor was used. The centrifugation speed was set at 35,000 rpm (i.e., 90,500×g) and material loading as well as buffer flush rates were set at 5 ml/min. The banding time was set at 2 hours. A gradient of 25 ml of 25% w/v and 58 ml of 50% w/v iodixanol was prepared in PBS buffer containing 0.1M sodium citrate and 3M NaCl. After the centrifugation was run, twenty-four (24) fractions of 5 ml each were collected. In addition, five (5) fractions of flow through were also collected to determine the distribution of the rAAV in the flow through.

Figure 25:
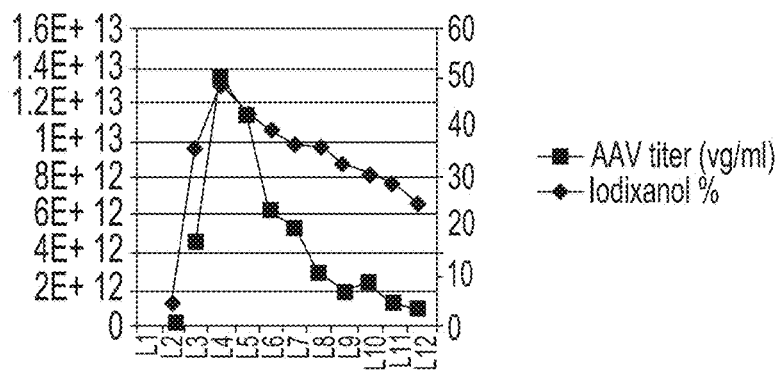
FIG. 25 is a graph illustrating the results of Experiment L.
Figure 26:
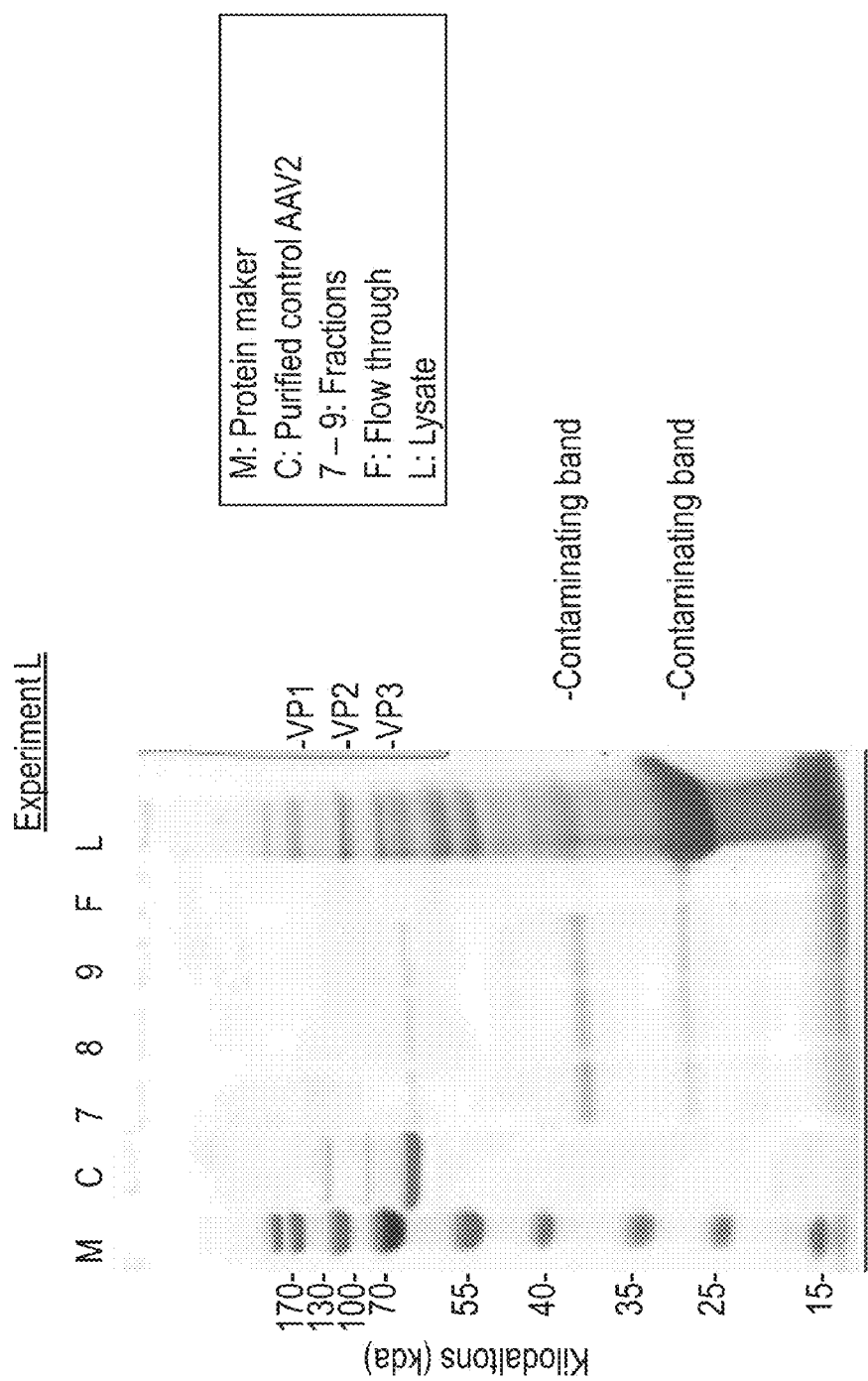
FIG. 26 is an image of SDS-PAGE and SimplyBlue™ staining of the fractions of Experiment L in FIG. 25.

The results are shown in FIGS. 25 and 26. It is noted that the recovery was 38%. Since the rAAV in the fractions contain high salt, and the rAAV titer in the fraction was low, desalting was performed only for fractions 7, 8, and 9, flow through, and lysate, and used for SDS-PAGE and staining assays of FIG. 26. It is also noted that the results of Experiment L appear to include at least some effects resulting from degradation of the lysate from storage. However, the results of FIG. 26 appear to indicate that that addition of 3M NaCl to the continuous flow gradient was not capable of removing the predictable contaminating bands from the rAAV in a single step centrifugation.

Experiment M

Another 1,000 ml culture in the same Lot#15-219 was used to prepare 100 ml lysate, but was prepared fresh unlike the frozen lysate discussed above in Experiment L. After clarification, caesium chloride was added to 1×PBS containing 100 mM sodium citrate to a concentration of 20% w/v. Wash buffer and iodixanol were also prepared to contain 0.1M sodium citrate and 20% w/v caesium chloride. The centrifugation parameters were exactly the same as in experiment L except this time the lysate was diluted by 40 ml of wash buffer during pump priming.

Figure 27:
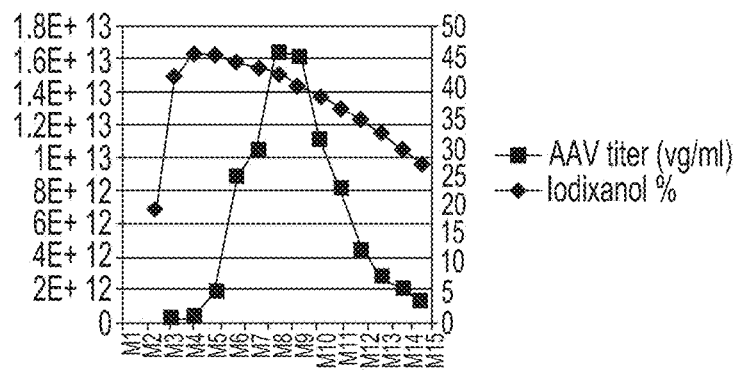
FIG. 27 is a graph illustrating the results of Experiment M.
Figure 28:
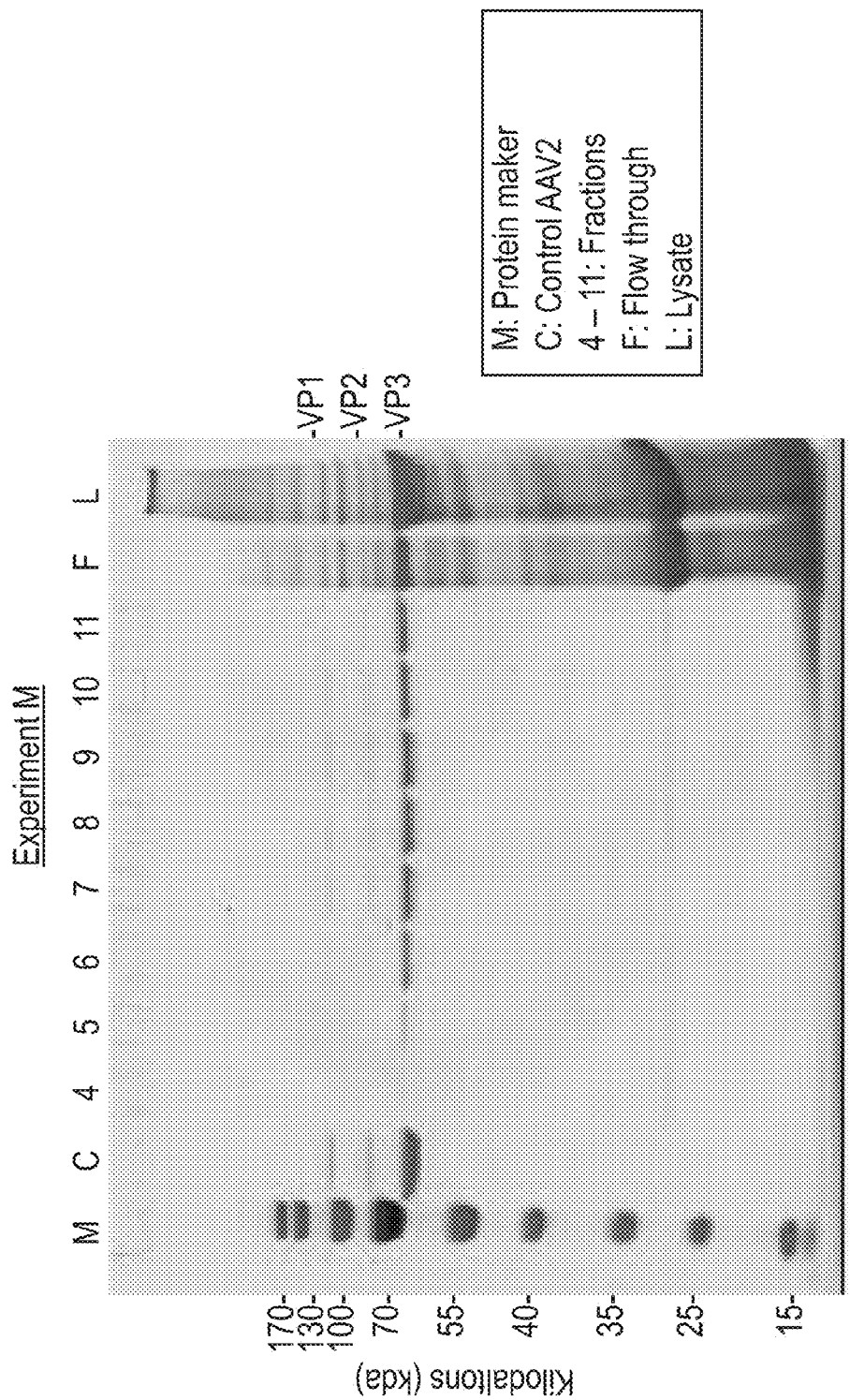
FIG. 28 is an image of SDS-PAGE and SimplyBlue™ staining of the fractions of Experiment M in FIG. 27.

The results are shown in FIGS. 27 and 28. This time the rAAV titer was high. In the lysate the titer of 1.3ge+13vg/ml was detected and a total of 1.95e+15vg were loaded in the purification process. The SDS-PAGE analysis of FIG. 28 indicates that the majority of the contaminants, including the predictable contaminant, were removed from the rAAV, in Lanes M4 through M14, after the single continuous flow centrifugation. Stated another way, the fractions in Lanes M4 through M14 include the target vector in pure form. Here, about 62% of the rAAV loaded was lost to the flow through and the yield of pure rAAV vector from Lanes M4 through M14 of pure vector was 21% of the rAAV loaded.

Based on SDS PAGE gel analysis, the rAAV vectors from collected fractions were pure with trace contaminating bands as shown in FIG. 28. These results indicate that by adding 20% w/v caesium chloride as a modifier to the iodixanol gradient, rAAV can be purified in one step with this continuous flow centrifugation method.

Experiment N

Figure 29:
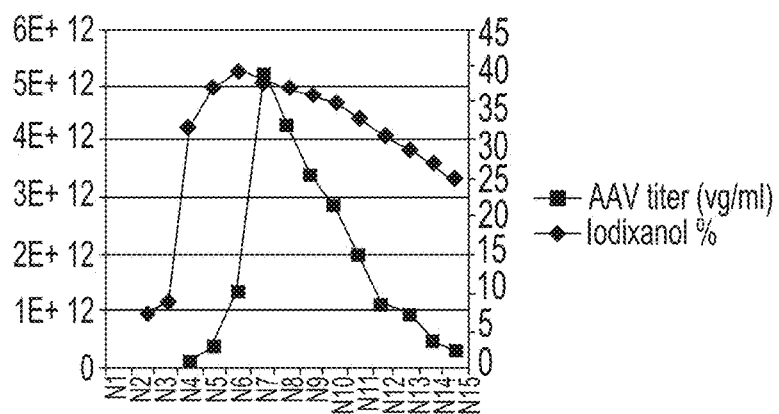
FIG. 29 is a graph illustrating the results of Experiment N.

A one-liter cell culture was used to prepare lysate and used in the experiment. The iodixanol gradients were prepared in PBS buffer containing 100 mM sodium citrate, 1% w/v Triton® X-100. The same buffer was used as wash buffer. The centrifugation parameters were exactly the same as in experiment L except this time the lysate was diluted by 40 ml of wash buffer during pump priming and 20% w/v CsCl and 1% w/v Triton® X-100 were added to all solutions. The results are shown in FIGS. 29 and 30.

Figure 30:
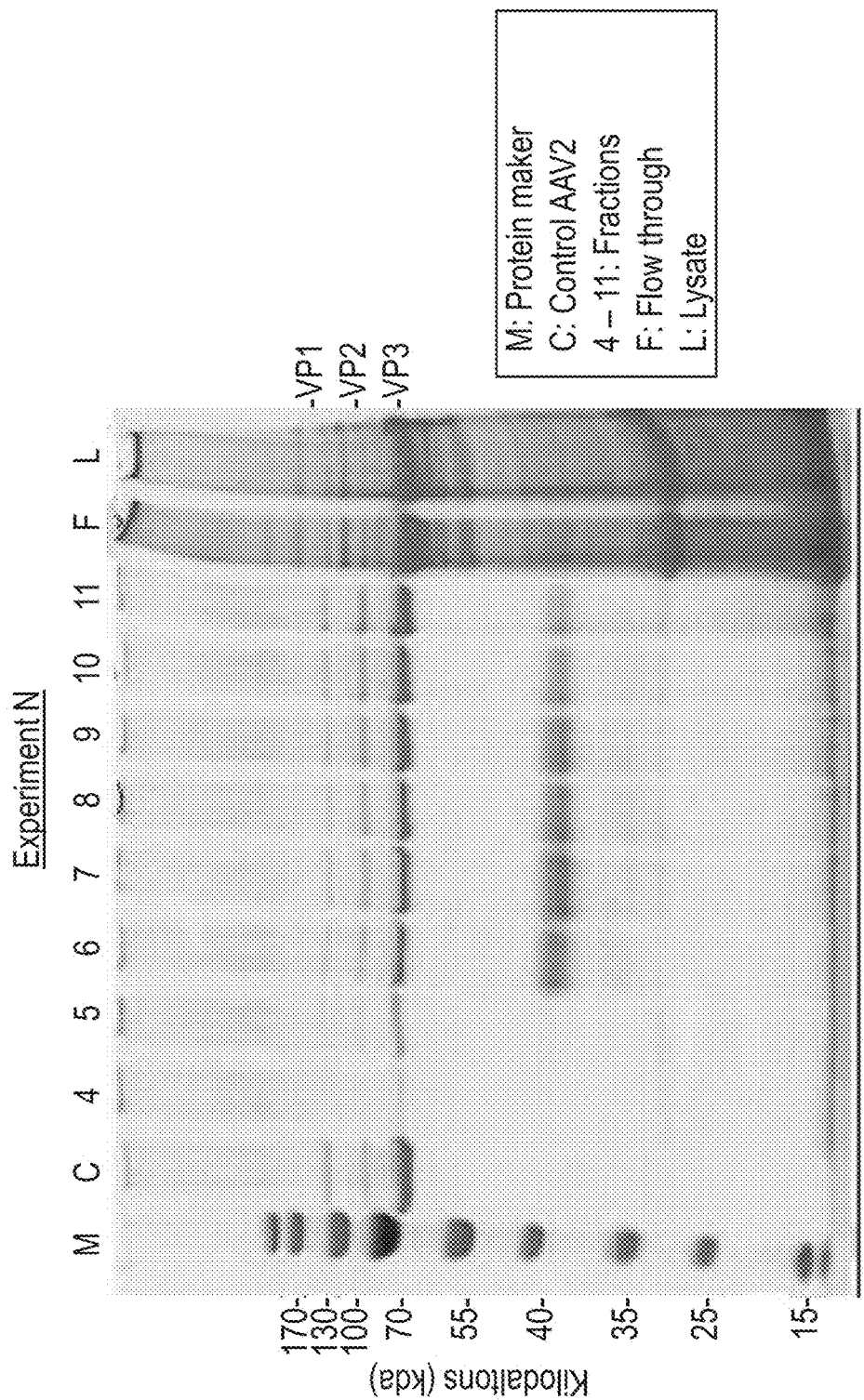
FIG. 30 is an image of SDS-PAGE and SimplyBlue™ staining of the fractions of Experiment N in FIG. 29.

The SDS-PAGE analysis of FIG. 30 indicates that the majority of the contaminants were removed from the rAAV, in Lanes N4 and N5, after the single continuous flow centrifugation. Stated another way, the fractions in Lanes N4 and N5 include the target vector in pure form. The fractions in Lanes N6 through N11 showed the predictable contaminant at about 40 kDa. Here, about 39% of the rAAV loaded was lost to the flow through and the recovery in fractions N4 through N15 was 24% of the rAAV loaded.

The result indicates that adding 1% w/v Triton® X-100 did not increase the rAAV recovery and negatively affected the purity of rAAV as shown in FIG. 30.

Figure 31:
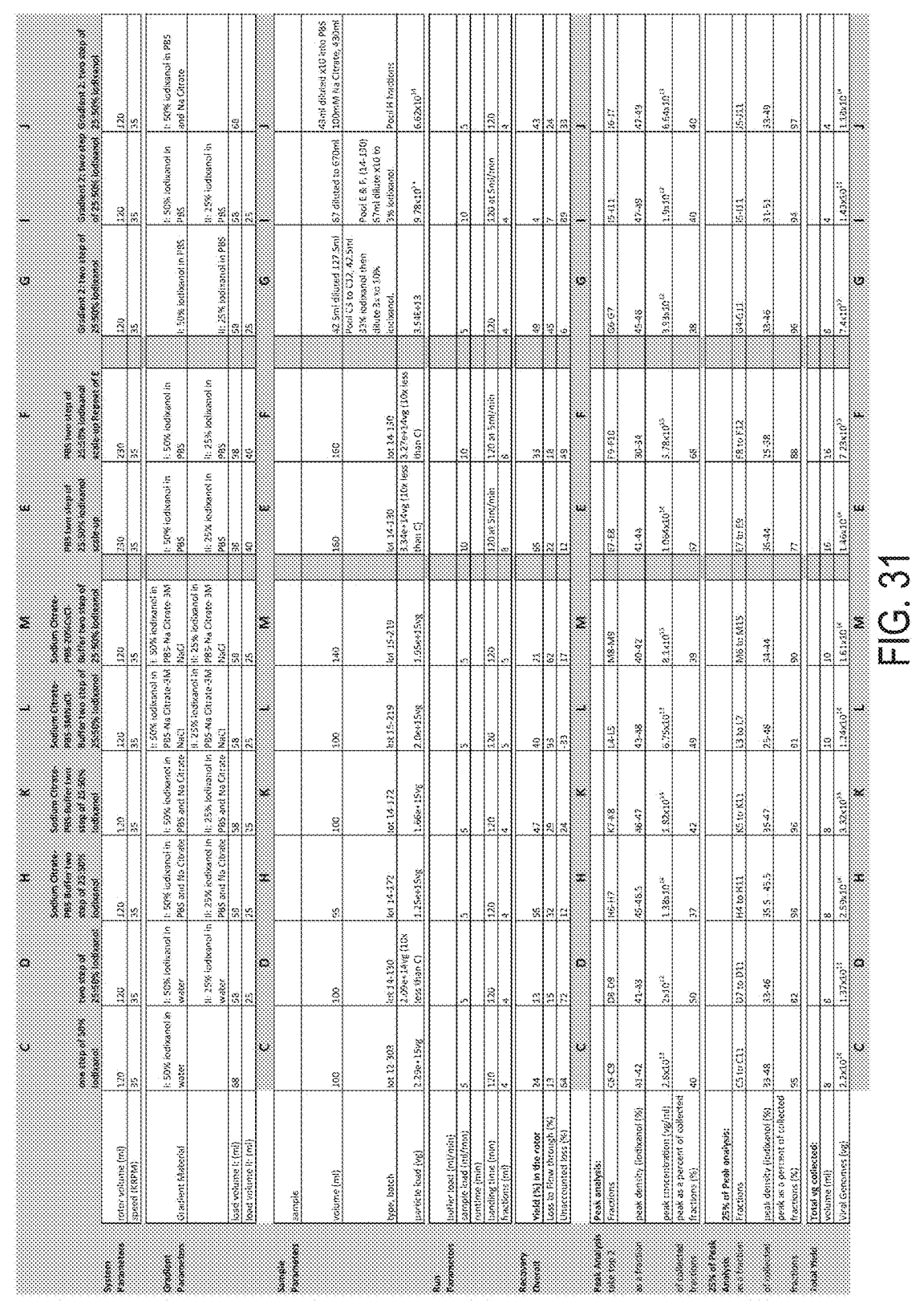

In order to better understand the results of the various experiment discussed above, FIG. 31 was prepared to compare Experiments C, D, H, K, L, M, E, G, I and J.

Centrifugation exploits the sedimentation differential between the target vector and the contaminants to effect a separation. In the case of AAV and rAAV, their sedimentation rate is fairly rapid in comparison to most soluble proteins, due to their relatively large size. Using continuous flow centrifugation, during the high speed operation of the machine the material can be introduced to the rotor and, having selected the appropriate flow rate, the target vector can be captured in the density gradient.

Correct selection of the flow rate is required to ensure adequate capture of the target vector and minimize losses of the target vector to the flow through. Also, the flow rate must be sufficiently high to exclude contaminants from rapidly accumulating in the density gradient. This continuous flow centrifugation, when optimized, can effect a significant purification leading to more than 90% of the contaminants passing through the rotor during high speed centrifugation and only a small proportion of the contaminants being captured in the density gradient. The design of the density gradient within the rotor can be optimized to allow for a concentrated accumulation of the target vector and effective separation from the contaminants that will inevitably enter the density gradient within the rotor during processing. The benefits of continuous flow centrifugation are that the material volume is not limited by the rotor volume. The feed material is continuously supplied during high speed operation and this process only needs to end when the density gradient is saturated with target vector. This can occur, depending on the feed stream, after upwards of 5 to 50 rotor volumes of material have been processed. This purification effectively leads to a high reduction in volume of the material and at the same time a high separation of target vector from the contaminants and can lead to increases in purification factor of 100 fold.

Experiments A and B were run to establish if the CsCl gradient used in a batch gradient operation could be transferred to a continuous flow operation. However, it was determined that a CsCl gradient does not provide for a gradient that can be used to purify rAAV using continuous flow centrifugation.

Other gradient media were therefore experimentally observed. In Experiment C, the use of a one-step gradient of 0% gradient i.e. water, and a 50% iodixanol gradient solution was made. The resulting purification achieved a separation of the target vector from the bulk of the contaminants that are found within the material. From the SDS PAGE analysis the target vector (VP1, VP2 and VP3), are seen clearly in the density gradient at higher concentration of 44 to 48% iodixanol (1.4066 to 1.4111 g/cm$^3$) and were seen to be essentially pure. Target vector not yet reaching this density range i.e. still in a rate zonal separation rather than in an isopycnic banding point are seen in less dense fractions having a peak density at 41% iodixanol (1.3999 g/cm3). The expectation from the known sedimentation of the rAAV in iodixanol is that the final position of the rAAV would be at about 48% iodixanol.

It is believed that the results of Experiment C indicate that the process of sedimentation is still active as the iso-dense layer is not reached for all or most of the target vector present in the density gradient. It is expected that the peak of a target vector will spread over the actual buoyant density of that target vector.

In the lower density fractions, contaminants are illustrated in the SDS PAGE one of which at approximately 38 kDa appears to occur in proportion to the target vector (VP1, VP2, and VP3). This can be said to be a 'predictable' or 'co-purifying' contaminant. Other contaminants seen throughout the same fractions e.g. around the 25 kDa range appear to have a concentration that increase as the density gradient decreases and therefore are believed to accumulate in a way that does not appear to have a relationship with the target vector.

It was determined by the present application from Experiment C that pure rAAV can be achieved in a one-step purification process using the AW Promatix 1000™ centrifuge. Although the yield from the purest fractions, when compared to the Control, does not amount to the major portion of the rAAV collected in the density gradients.

The present application then considered further work with the aim to resolve the contaminants further away from the rAAV as the contaminants have significant overlap with the peak seen in fractions C9 and C10. This led to Experiment D, employing a second layer of iodixanol at a lower density. The aim was to have a gradient with more volume available at a lower density so that the contaminant would take longer to travel through the density gradient and therefore there is a better resolution between the rapidly moving rAAV and the slower moving smaller contaminants.

In Experiment D a 25% iodixanol and a 50% iodixanol were used. From the SDS PAGE analysis this appeared to have removed a small amount of contaminants, in this case the loading material was not considered to be of a high enough concentration and losses during the purification process were high and so yield was low.

It should be recognized that the lower concentration limit of 25% and the upper concentration limit of 50% in Experiment D were selected to test potential outer boundaries for the two-layer separation. However, it is contemplated by the present disclosure for other combinations of iodixanol concentrations to be used provided that the lower concentration limit is high enough to avoid the iodixanol from washing out of the rotor and the higher concentration limit should remain within the limits of where the iodixanol remains in solution. Moreover, it is contemplated by the present disclosure for the density gradient to have more than two-levels at concentrations between 1% and 60%.

To further evaluate the performance of the two-level gradient in the 25%:50% concentrations, a buffering system was added to stabilize the target vector and so aid in the yield recovery and give a better purification.

In Experiment E, two factors were altered. A buffer system of PBS was employed and a larger rotor (double the size of the earlier tests) was used. This was to compare the gradient profile and performance during scale up. Results from E indicate a high recovery of 65%, demonstrating that the PBS buffering was increasing the stability of the product. Also, the overall yield was high with a pool of 16 ml containing $1.46 \times 10^{14}$ viral genomes (vg) collected. From the SDS PAGE analysis the peak fraction does not appear to have a significantly improved purity when compared to Experiment C.

To further improve purity, the present application considered to repeat the centrifugation using a pool of materials from a previously centrifuged product. To this end fractions from Experiment C were pooled then diluted to decrease the overall density. This dilution was made to minimize the loss to flow through that may occur when loading materials as a more similar density to that of the stationary gradient. In Experiment G the results of this separation can be seen. The yield was 49% and from the SDS PAGE it appeared that a significant proportion of the contaminants had been removed. With a yield of 49% on the second run and a yield of 24% on the first run then on overall recovery of only 12% was achieved.

Experiment H was conducted with 100 mM sodium citrate added to the buffer, which is believed by the present application to contribute to the stability of the rAAV and therefore may be effective to improve the yields during purification. Advantageously, the findings showed that a significant improvement in yield occurred as compared to Experiment C—as a 56% recovery was achieved with the target vector distributed from 35 to 47% iodixanol. The peak fraction being around 46-47% iodixanol. By SDS PAGE this peak fraction is now substantially pure in comparison to the Control and the peak only appears to have a predictable contaminant at about 38 kDa present.

Experiment K was conducted to repeat Experiment H so as to confirm the result. Indeed, a similar result was achieved for purity and for yield with 47% being achieved. The predictable contaminant was still present and is considered by the present disclosure to be a reproducible feature of purification using iodixanol as a density gradient medium.

Experiment G and Experiment I pooled the fractions from Experiment E and were then diluted to reduce the material density and run on a second essentially identical density gradient. Although the peak of the product was present at the correct density of above 44% iodixanol the recovery was low. SDS PAGE did not show in this case an effective purification and the predictable contaminants remained.

Experiment J gave a similar result, which indicated that a second centrifugation does not provide additional purification and leads to significant losses of rAAV. Stated another way, Experiments G, I and J illustrated that additional centrifugation steps were not effective at removing predictable contaminant while retaining a reasonable yield.

The present application then conducted further small scale experimentation to examine the 38 kDa predictable contaminant and the association with the rAAV. To confirm the hypothesis of the present application that these contaminates are not a feature of continuous flow centrifugation methodology, the iodixanol gradient was transferred back to a batch tube rotor and the same experimental conditions used as for a CsCl density gradient but with the exchange of iodixanol as the density gradient medium. The same separation of the predictable contaminant was seen in the SDS PAGE from this tube experiment. This is believed to confirm the hypothesis of the present application that the predictable contaminant is/are a function of the iodixanol density gradient method and not of the continuous flow centrifugation method.

To look at the disassociation of predictable contaminant from target vector, the present application used dialysis with 1000 kDa or 300 kDa filters which would retain the rAAV but should have allowed contaminants to be released. The SDS PAGE analysis did not illustrate a removal of the predictable contaminant by dialysis alone. From these results, it was hypothesized that the association between the target vector and the predictable contaminant was significant and could be affected by altering buffering conditions.

Therefore, the present application further processed fractions from a first centrifugation on the continuous flow centrifuge on a second batch gradient to examine the effect of addition of either CsCl or NaCl to the material. This demonstrated, as shown in the SDS PAGE that the addition of either CsCl to a 1.38 $g/cm^3$ density or 3M NaCl effectively removed the co-contaminants in an experimental tube rotor protocol.

The parameters discovered in the batch tube rotor tests with CsCl and NaCl were examined further using the AW Promatix 1000™. Experiment L used the same parameters as previously but with the inclusion of 3M NaCl in the buffers. Although a high yield of $1.24 \times 10^{14}$ viral genomes (vg) was achieved and the rAAV was found at the iso-dense layer i.e. 43 to 48% iodixanol the previously identified predictable contaminant remained. Although all other contaminants were removed.

Experiment L substituted the NaCl for the CsCl and in this case from the SDS PAGE analysis it can be seen that the predictable contaminant is substantially removed from all fractions of the density gradient. This leaves the rAAV essentially pure using one process purification step from a lysate (i.e., material). The only limiting factor was a decrease in the overall yield to 21% in the density gradient. This yielded at the peak $1.61 \times 10^{14}$ viral genomes (vg).

One further study to examine if the predictable contaminant would be effectively removed by a surfactant demonstrated this is not the case even in the presence of the CsCl used in experiment L. In this latter case the yield remained the same as in the CsCl alone density gradient but had lost the previously achieved purity.

In conclusion, the present application provides a one-step continuous flow purification of AAV and/or rAAV in an unmodified gradient—in a manner that results in separation of the target vector together with the predictable contaminant as seen in at least Experiments E, H, and K with yields of 65%, 55%, and 47%, respectively. In some embodiments, the predictable contaminant can be removed in a subsequent purification step, which occurs after the continuous flow centrifugation step. Moreover, the present application provides a one-step continuous flow purification of AAV and/or rAAV in a modified gradient—in a manner that results in separation of the target vector that is separated from the predictable contaminant as seen in at least Experiment M with a yield of 21%.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of disclosure herein.

What is claimed is:

1. A method of purifying a viral vector, comprising:
   loading a nonionic density gradient into a continuous flow centrifuge rotor;
   loading a material including the viral vector into the continuous flow centrifuge rotor, while the continuous flow centrifuge rotor is rotating in the presence of a modifying agent that is sufficient to separate the viral vector and a predictable contaminant from the material in the nonionic density gradient, wherein the modifying agent comprises CsCl at a concentration of up to 40% w/v; and
   unloading the separated viral vector from the continuous flow centrifuge rotor.

2. The method of claim 1, wherein the material is a lysate comprising the viral vector.

3. The method of claim 1, wherein the nonionic density gradient comprises iodixanol in a solution with an aqueous buffer.

4. The method of claim 3, wherein the aqueous buffer comprises phosphate-buffered saline (PBS).

5. The method of claim 1, wherein the nonionic density gradient comprises iodixanol in a solution of between 1 and 60 percent weight per volume (% w/v) with an aqueous buffer.

6. The method of claim 1, wherein the nonionic density gradient comprises iodixanol in a solution of between 25 and 50% w/v with an aqueous buffer.

7. The method of claim 6, wherein the iodixanol comprises a two-layer stepped gradient comprising a 25% w/v layer and a 50% w/v layer.

8. The method of claim 6, wherein the separated viral vector comprises at least 47% of the viral vector in the material.

9. The method of claim 8, wherein the separated viral vector comprises up to 65% of the viral vector in the material.

10. The method of claim 1, wherein the modifying agent is present in a concentration to provide sufficient ionic potential to alter any co-purifying interaction between the predicable contaminant and the material.

11. The method of claim 1, wherein the nonionic density gradient comprises the modifying agent.

12. The method of claim 1, wherein the step of rotating the continuous flow centrifuge rotor further comprises rotating while using a flow through buffer, the flow through buffer comprising the modifying agent.

13. The method of claim 1, wherein the material comprises the modifying agent.

14. The method of claim 1, wherein the modifying agent further comprises an agent selected from the group consisting of potassium chloride (KCl), sodium chloride (NaCl), Percoll®, iohexol, metrizamide, Sucrose, Glycerol, Glucose, potassium Bromide (KBr), and any combinations thereof.

15. The method of claim 1, wherein the modifying agent comprises CsCl at a concentration of 20% w/v.

16. The method of claim 15, wherein the separated viral vector comprises at least 21% of the viral vector in the material.

17. The method of claim 1, wherein the viral vector comprises at least one of adeno-associated virus (AAV) and recombinant adeno-associated virus (rAAV).

18. The method of claim 1, wherein the step of loading the nonionic density gradient into the continuous flow centrifuge rotor comprises a static gradient loading or a dynamic gradient loading.

19. The method of claim 1, wherein the step of unloading comprises a static gradient unloading or a dynamic gradient unloading.

20. The method of claim 1, further comprising orienting the nonionic density gradient prior to loading the material into the continuous flow centrifuge rotor.

21. The method of claim 1, wherein the step of loading the nonionic density gradient into the continuous flow centrifuge rotor comprises loading a mixed gradient or a linear gradient.

22. A method of purifying a viral vector, comprising:
    loading a nonionic density gradient into a continuous flow centrifuge rotor;
    loading a material including the viral vector into the continuous flow centrifuge rotor, wherein the viral vector comprises at least one of AAV and rAAV, while the continuous flow centrifuge rotor is rotating in the presence of a modifying agent that is sufficient to separate the viral vector and a predicable contaminant from the material in the nonionic density gradient, wherein the modifying agent comprises CsCl at a concentration of up to 40% w/v; and unloading the separated viral vector from the continuous flow centrifuge rotor.

23. The method of claim 22, wherein the nonionic density gradient comprises the modifying agent.

24. The method of claim 22, wherein the step of rotating the continuous flow centrifuge rotor further comprises rotating while using a flow through buffer, the flow through buffer comprising the modifying agent.

25. The method of claim 22, wherein the material comprises the modifying agent.

26. A method of purifying a viral vector, comprising:
loading a nonionic density gradient into a continuous flow centrifuge rotor, the nonionic density gradient comprising iodixanol in a solution of between 25 and 50% w/v and PBS;

loading a material including the viral vector into the continuous flow centrifuge rotor, wherein the viral vector comprises at least one of AAV and rAAV, while the continuous flow centrifuge rotor is rotating in the presence of CsCl at a concentration of up to 40% w/v in a manner sufficient to separate the viral vector from the material in the nonionic density gradient; and unloading the separated viral vector from the continuous flow centrifuge rotor, wherein the separated viral vector comprises at least 21% of the viral vector in the material.

27. The method of claim 26, wherein the nonionic density gradient comprises the CsCl.

28. The method of claim 26, wherein the step of rotating the continuous flow centrifuge rotor further comprises rotating while using a flow through buffer, the flow through buffer comprising the CsCl.

29. The method of claim 26, wherein the material comprises the CsCl.

30. A density gradient for continuous flow centrifugation, comprising:
iodixanol in an amount selected from the group consisting of 25 and 50% w/v;
CsCl in an amount up to 40% w/v; and
an aqueous buffer.

31. The density gradient of claim 30, further comprising 100 mM sodium citrate.

32. The density gradient of claim 30, wherein the aqueous buffer comprises PBS.

33. The density gradient of claim 32, further comprising 100 mM sodium citrate.

34. The density gradient of claim 30, wherein the amount of iodixanol is 25% w/v.

35. The density gradient of claim 30, wherein the amount of iodixanol is 50% w/v.

36. The density gradient of claim 30, wherein the amount of CsCl is 20% w/v.

* * * * *